United States Patent [19]
Manoharan et al.

[11] Patent Number: 6,147,200
[45] Date of Patent: Nov. 14, 2000

[54] 2'-O-ACETAMIDO MODIFIED MONOMERS AND OLIGOMERS

[75] Inventors: Muthiah Manoharan; Andrew M. Kawasaki, both of Carlsbad; Phillip Dan Cook, Fallbrook; Allister S. Fraser; Thazha P. Prakash, both of Carlsbad, all of Calif.

[73] Assignee: Isis Pharmaceuticals, Inc., Carlsbad, Calif.

[21] Appl. No.: 09/378,568

[22] Filed: Aug. 19, 1999

[51] Int. Cl.[7] .................................................. C07H 21/02
[52] U.S. Cl. ..................... 536/23.1; 536/24.3; 536/24.5; 536/25.1; 536/25.34; 536/26.7; 536/26.8; 536/27.61; 536/27.8; 536/27.81; 536/28.5; 536/28.53; 514/44
[58] Field of Search ............................. 536/23.1, 24.3, 536/24.5, 25.1, 25.34, 26.7, 26.8, 27.6, 27.61, 27.8, 27.81, 28.5, 28.53

[56] References Cited

U.S. PATENT DOCUMENTS

| | | |
|---|---|---|
| Re. 34,069 | 9/1992 | Köster et al. . |
| 3,687,808 | 8/1972 | Merigan et al. . |
| 4,415,732 | 11/1983 | Caruthers et al. . |
| 4,458,066 | 7/1984 | Caruthers et al. . |
| 4,469,863 | 9/1984 | Ts'o et al. . |
| 4,500,707 | 2/1985 | Caruthers et al. . |
| 4,668,777 | 5/1987 | Caruthers et al. . |
| 4,725,677 | 2/1988 | Köster et al. . |
| 4,845,205 | 7/1989 | Huynh Dinh et al. . |
| 4,973,679 | 11/1990 | Caruthers et al. . |
| 4,981,957 | 1/1991 | Lebleu et al. . |
| 5,034,506 | 7/1991 | Summerton et al. ............. 528/391 |
| 5,118,800 | 6/1992 | Smith et al. . |
| 5,124,047 | 6/1992 | Quach et al. ..................... 210/699 |
| 5,130,302 | 7/1992 | Spielvogel et al. ................ 514/45 |
| 5,132,418 | 7/1992 | Caruthers et al. . |
| 5,134,066 | 7/1992 | Rogers et al. ..................... 435/91 |
| 5,138,045 | 8/1992 | Cook et al. . |

(List continued on next page.)

FOREIGN PATENT DOCUMENTS

| | | |
|---|---|---|
| 0 216 860 B1 | 10/1992 | European Pat. Off. . |
| WO 89/12060 | 12/1989 | WIPO . |
| WO 90/15065 | 12/1990 | WIPO . |
| WO 91/08213 | 6/1991 | WIPO . |
| WO 91/10671 | 7/1991 | WIPO . |
| WO 91/15500 | 10/1991 | WIPO . |
| WO 91/18997 | 12/1991 | WIPO . |
| WO 92/02258 | 2/1992 | WIPO . |
| WO 92/03568 | 3/1992 | WIPO . |
| WO 92/05186 | 4/1992 | WIPO . |
| WO 92/19637 | 11/1992 | WIPO . |
| WO 92/20822 | 11/1992 | WIPO . |
| WO 92/20823 | 11/1992 | WIPO . |
| WO 92/22651 | 12/1992 | WIPO . |
| WO 93/07883 | 4/1993 | WIPO . |

OTHER PUBLICATIONS

Agrawal et al. (eds.), "Methods of Molecular Biology", in *Protocols for Oligonucleotide Conjugates*, Agrawal, S. (ed.), Humana Press, New Jersey, 1994, vol. 26, 1–72.

Altmann, K. et al., "Second Generation of Antisense Oligonucleotides: From (Apr. 1996). Nuclease Resistance to Biological Efficacy in Animals," *Chimia*, 1996, 50, 168–176.

(List continued on next page.)

*Primary Examiner*—Gary Geist
*Assistant Examiner*—L. Eric Crane
*Attorney, Agent, or Firm*—Woodcock Washburn Kurtz Mackiewicz & Norris LLP

[57] ABSTRACT

Nucleosidic monomers and oligomeric compounds prepared therefrom are provided. Also provided is a novel method of deprotection of oligomeric compounds. Oligomeric compounds having at least one 2'-O-acetamido modified nucleosidic monomer are expected to have increased nuclease resistance and binding affinity to a complementary strand of nucleic acid. Such oligomeric compounds are useful for diagnostics and other research purposes, for modulating the expression of a protein in organisms, and for the diagnosis, detection and treatment of other conditions responsive to oligonucleotide therapeutics.

46 Claims, 2 Drawing Sheets

| Compound # | Bx | E₁ | E₂ |
|---|---|---|---|
| 26 | 5-methyluracil | methyl | methyl |
| 27, 28 | 5-methyluracil | H | polyamine |
| 29 | 5-methyluracil | H | polpeptide |
| 30 | 5-methyluracil | H | linked-cholesterol |
| 31 | 5-methyluracil | H | linked folic acid |
| 43 | 5-methyluracil | H | -CH$_2$CH$_2$-S-CH$_3$ |

U.S. PATENT DOCUMENTS

| | | | |
|---|---|---|---|
| 5,166,195 | 11/1992 | Ecker | 514/44 |
| 5,175,273 | 12/1992 | Bischofberger et al. | |
| 5,210,264 | 5/1993 | Yau | 558/167 |
| 5,214,134 | 5/1993 | Weis et al. | 536/25.3 |
| 5,218,105 | 6/1993 | Cook et al. | 536/25.31 |
| 5,223,618 | 6/1993 | Cook et al. | 544/276 |
| 5,242,906 | 9/1993 | Pagano et al. | 514/44 |
| 5,248,670 | 9/1993 | Draper et al. | 514/44 |
| 5,278,302 | 1/1994 | Caruthers et al. | 536/24.5 |
| 5,319,080 | 6/1994 | Leumann | 536/27.1 |
| 5,321,131 | 6/1994 | Agrawal et al. | 536/25.34 |
| 5,348,868 | 9/1994 | Reddy et al. | 435/91.1 |
| 5,359,044 | 10/1994 | Cook et al. | 536/23.1 |
| 5,367,066 | 11/1994 | Urdea et al. | 536/24.3 |
| 5,378,825 | 1/1995 | Cook et al. | 536/25.34 |
| 5,386,023 | 1/1995 | Sanghvi et al. | 536/25.3 |
| 5,393,878 | 2/1995 | Leumann | 536/28.2 |
| 5,432,272 | 7/1995 | Benner | 536/25.3 |
| 5,434,257 | 7/1995 | Matteucci et al. | 536/24.3 |
| 5,442,049 | 8/1995 | Anderson et al. | 536/24.5 |
| 5,446,137 | 8/1995 | Maag et al. | 536/23.1 |
| 5,455,233 | 10/1995 | Spielvogel et al. | 514/44 |
| 5,457,187 | 10/1995 | Gmeiner et al. | 536/25.5 |
| 5,457,189 | 10/1995 | Crooke et al. | 536/24.5 |
| 5,457,191 | 10/1995 | Cook et al. | 536/27.13 |
| 5,459,255 | 10/1995 | Cook et al. | 536/27.13 |
| 5,466,677 | 11/1995 | Baxter et al. | 514/44 |
| 5,466,786 | 11/1995 | Buhr et al. | 536/26.26 |
| 5,470,967 | 11/1995 | Huie et al. | 536/24.3 |
| 5,484,908 | 1/1996 | Froehler et al. | 536/24.31 |
| 5,489,677 | 2/1996 | Sanghvi et al. | 536/22.1 |
| 5,502,177 | 3/1996 | Matteucci et al. | 536/26.6 |
| 5,506,351 | 4/1996 | McGee | 536/55.3 |
| 5,510,239 | 4/1996 | Baracchini, Jr. et al. | 435/6 |
| 5,510,476 | 4/1996 | Ravikumar et al. | 536/25.31 |
| 5,514,577 | 5/1996 | Draper et al. | 435/238 |
| 5,514,785 | 5/1996 | Van Ness et al. | 536/22.1 |
| 5,514,786 | 5/1996 | Cook et al. | 536/23.1 |
| 5,514,788 | 5/1996 | Bennett et al. | 536/23.1 |
| 5,514,789 | 5/1996 | Kempe | 536/25.4 |
| 5,518,651 | 5/1996 | Reddy et al. | 252/193 |
| 5,519,126 | 5/1996 | Hecht | 536/24.3 |
| 5,519,134 | 5/1996 | Acevedo et al. | 544/243 |
| 5,523,389 | 6/1996 | Ecker et al. | 536/23.1 |
| 5,525,711 | 6/1996 | Hawkins et al. | 536/22.1 |
| 5,530,389 | 6/1996 | Rieder | 327/156 |
| 5,541,307 | 7/1996 | Cook et al. | 536/23.1 |
| 5,543,507 | 8/1996 | Cook et al. | 536/23.1 |
| 5,552,540 | 9/1996 | Haralambidis | 536/25.34 |
| 5,563,255 | 10/1996 | Monia et al. | 536/24.31 |
| 5,567,811 | 10/1996 | Misiura et al. | 536/25.34 |
| 5,571,902 | 11/1996 | Ravikumar et al. | 536/22.1 |
| 5,576,208 | 11/1996 | Monia et al. | 435/240.2 |
| 5,576,302 | 11/1996 | Cook et al. | 514/44 |
| 5,576,427 | 11/1996 | Cook et al. | 536/23.1 |
| 5,578,718 | 11/1996 | Cook et al. | 536/27.21 |
| 5,580,767 | 12/1996 | Cowsert et al. | 435/172.3 |
| 5,582,972 | 12/1996 | Lima et al. | 435/6 |
| 5,582,986 | 12/1996 | Monia et al. | 435/6 |
| 5,587,361 | 12/1996 | Cook et al. | 514/44 |
| 5,587,469 | 12/1996 | Cook et al. | 536/23.1 |
| 5,591,600 | 1/1997 | Ecker | 435/69.1 |
| 5,591,623 | 1/1997 | Bennett et al. | 435/240.2 |
| 5,591,720 | 1/1997 | Anderson et al. | 514/44 |
| 5,591,722 | 1/1997 | Montgomery et al. | 514/45 |
| 5,594,121 | 1/1997 | Froehler et al. | 536/23.5 |
| 5,596,091 | 1/1997 | Switzer | 536/24.5 |
| 5,597,909 | 1/1997 | Urdea et al. | 536/24.3 |
| 5,610,300 | 3/1997 | Altmann et al. | 544/244 |
| 5,614,617 | 3/1997 | Cook et al. | 536/23.1 |
| 5,623,065 | 4/1997 | Cook et al. | 536/23.1 |
| 5,627,053 | 5/1997 | Usman et al. | 435/91.1 |
| 5,639,873 | 6/1997 | Barascut et al. | 536/25.3 |
| 5,646,265 | 7/1997 | McGee | 536/25.34 |
| 5,658,873 | 8/1997 | Bertsch-Frank et al. | 510/375 |
| 5,670,633 | 9/1997 | Cook et al. | 536/23.1 |
| 5,681,941 | 10/1997 | Cook et al. | 536/23.1 |
| 5,700,920 | 12/1997 | Altmann et al. | 536/221 |
| 5,750,672 | 5/1998 | Kempe | 536/25.31 |
| 5,750,692 | 5/1998 | Cook et al. | 544/253 |
| 5,792,847 | 8/1998 | Buhr et al. | 536/23.1 |
| 5,817,781 | 10/1998 | Swaminathan et al. | 536/22.1 |
| 5,859,221 | 1/1999 | Cook et al. | 536/23.1 |

OTHER PUBLICATIONS

Altmann, K. et al., "Second Generation Antisense Oligonucleotides—Inhibition of Pkc–1 And c–RAF Kinase Expression by Chimeric Oligonucleotides Incorporating 6–Substituted Carbocyclic Nucleosides and 2'–O–Ethylene Glycol Substituted Ribonucleosides," *Nucleosides & Nucleotides*, 1997, 16(7–9), 917–926.

Altmann, K. et al., "Second–Generation Antisense Oligonucleotides: Structure–Activity Relationships and the Design of Improved Signal–Transduction Inhibitors", *Biochem. Soc. Trans.*, 1996, 24, 630–637.

Alul, R.H. et al., "Oxalyl–CPG: a labile support for synthesis of sensitive oligonucleotide derivatives", *Nucl. Acid. Res.*, 1991, 19, 1527–1532 (Iss. No. 7).

Arnott, S. et al., "Optimised Parameters for A–DNA and B–DNA", *Biochem. & Biophys. Res. Commun.*, 1972, 47, 1504–1510 (Iss. No. 6).

Baker, B.F. et al., "2'–O–(2–Methoxy)ethyl–modified Anti–intercellular Adhesion Molecule 1 (ICAM–1) Oligonucleotides Selectively Increase the ICAM–1 Translation Initiation Complex in Human Umbilical Vein Endothelial Cells", *J. Biol. Chem.*, 1997, 272, 11995–12000 (Jun. 5, 1992).

Beal, P. A. et al., "Second Structural Motif for Recognition of DNA by (Mar. 15, 1991). Oligonucleotide–Directed Triple–Helix Formation", *Science*, 1991, 251, 1360–1363.

Beaucage, S.L. et al., "Advances in the Synthesis of Oligonucleotides by the Phosphoramidite Approach", *Tetrahedron*, 1992, 48, 2223–2311 (Iss. No. 12).

Beaucage, S.L. et al., "Deoxynucleoside Phosphoramidites—A New Class of Key (Iss. No. 20). Intermediates for Deoxypolynucleotide Synthesis", *Tetra. Letts.*, 1981, 22, 1859–1862.

Bock, L. C. et al., "Selection of Single–Stranded DNA Molecules that Bind and Inhibit Human Thrombin," *Nature*, 1992, 355, 564–566 (Feb. 6, 1992).

Caruthers, M.H., "Synthesis of Oligonucleotides and Oligonucleotide Analogues", *Oligonucleotides: Antisense Inhibitors of Gene Expression*, 1989, Chapter 1, Cohen, J.S. (Ed.), CRC Press, Boca Raton, FL, 7–24.

Conte, M.R. et al., "Confirmational Properties and Thermodynamics of the RNA Duplex r(CGCAAAUUUGCG)2: Comparison with the DNA Analogue d(CG-CAAATTTGCG)2," *Nucl. Acids Res.*, 1997, 25(13), 2627–2634.

Cook, P.D., "Medicinal Chemistry of Antisense Oligonucleotides—future opportunities", *Anti–Cancer Drug Design*, 1991, 6, 585–607.

Coull, J.M. et al., "Synthesis and Characterization of a Carbamate–Linked Oligonucleoside", *Tetrahedron Letts.*, 1987, 28, 745–748 (Iss. No. 7).

Crooke, S. T., "Progress in Antisense Therapeutics," *Medicinal Research Reviews*, 1996, 16(4), 319–344.

Crooke, S.T. et al., "Pharmacokinetic Properties of Several Novel Oligonucleotide Analogs in mice,", *J. Pharmacol. Exp. Therapeutics,* 1996, 277, 923–937 (Iss. No. 2).

DeMesmaeker, A. et al., "Antisense Oligonucleotides", *Acc. Chem. Res.,* 1995, 28, 366–374 (Iss. No. 9).

Delgado, C. et al., "The Uses and Properties of PEG–Linked Proteins", *Crit. Rev. in Therapeutic Drug Carrier Sys.,* 1992, 9, 249–304 Iss. Nos. 3–4).

Divakar, K.J. et al., "4–(1,2,4–Triazol–1–ly)–and 4–(3–Nitro–1,2,4–triazol–1–yl)–1–(β–D–2,3,5–tri–O–acetylarabinofuranosyl) pyrimidin–2(1H)–ones. Valuable Intermediates in the Synthesis of Derivatives of 1–(β–D–Arabinofuranosyl)cytosine (Ara–C)", *J.C.S. Perkin I,* 1982, 1171–1176.

Egli, M. et al., "RNA Hydration: A Detailed Look," *Biochemistry,* 1996, 35, 8489–8494 (Iss. No. 26).

Englisch, U. et al., "Chemically Modified Oligonucleotides as Probes and Inhibitors", *Angew. Chem. Int. Ed. Eng.,* 1991, 30, 613–629 (Iss. No. 6, Jun. 1991).

Federoff, O. Y. et al., "Structure of a DNA: RNA Hybrid Duplex Why Rnase H Does Not Cleave Pure RNA," *J. Mol. Biol.,* 1993, 233, 509–523 (Issue No. 22).

Freier, S.M. et al., "The ups and downs of nucleic acid duplex stability: structure–stability studies on chemically–modified DNA:RNA duplexes", *Nucl. Acids Res.,* 1997, 25, 4429–4443 (Iss. No. 22).

Gait, M.J., "Oligoribonucleotides," *Antisense Research and Applications,* Crooke, S.T. et al., (eds.), CRC Press, Boca Raton, 1993, Chapter 16, 289–302.

Gonzalez, C. et al., "Structure and Dynamics of a DNA–RNA Hybrid Duplex with a Chral Phosphorothioate Moiety: NMR and Molecular Dynamics with Conventional and Time–Averaged Restraints," *Biochemistry,* 1995, 34, 4969–4982 (Iss. No. 15).

Griffin, L. C. et al., "In Vivo Anticoagulant Properties of a Novel Nucleotide–Based Thrombin Inhibitor and Demonstration of Regional Anticoagulation in Extracorporeal Circuits," *Blood,* 1993, 81, 3271–3276 (Iss. No. 12; Jun. 15, 1993).

Hamm, M. L. et al., "Incorporation of 2'–Deoxy–2'–mercaptocytidine into Oligonucleotides via Phosphoramidite Chemistry," *J. Org. Chem.,* 1997, 62, 3415–3420 (Iss. No. 10).

Hewitt, J.M. et al., "Structural Determination of Silicon–Containing Oligonucleotides by $^{1}H-^{29}Si$ Long–Range Heteronuclear Multiple Quantum Correlation NMR Spectroscopy", 1992, 11, 1661–1666 (Iss. No. 9).

Horton, N. C. et al., "The Structure of an RNA/DNA Hybrid: A Substrate of the Ribonuclease Activity of HIV–1 Reverse Transcriptase," *J. Mol. Biol.,* 1996, 264, 521–533.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.,* 1990, 55, 4693–4699 (Iss. No. 15).

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.,* 1990, 112, 1253–1254.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.,* 1990, 259, 327–330) (Jan., 1990).

Kamer, P.C.J. et al., "An Efficient Approach Toward the Synthesis of Phosphorothioate Diesters via the Schonberg Reaction", *Tetrahedron Letts.,* 1989, 30, 6757–6760 (Issue No. 48).

Kroschwitz, J.I., "Polynucleotides", *Concise Encyclopedia of Polymer Science and Engineering,* 1990, John Wiley & Sons, New York, 858–859.

Lane, A. N. et al., "NMR Assignments and Solution Conformation of the DNA–RNA Hybrid Duplex d(GTGAACT-T)–r(AAGUUCAC)," *Eur. J. Biochem.,* 1993, 215, 297–306.

Lesnik, E. A. et al., "Relative Thermodynamic Stability of DNA, RNA, and DNA: RNA Hybrid Duplexes: Relationship with Base Composition and Structure," *Biochemistry,* 1995, 34(34), 10807–10815.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.,* 1989, 86, 6553–6556 (Sep., 1989).

Manoharan, M. et al., "Lipidic Nucleic Acids", *Tetrahedron Letts.,* 1995, 36, 3651–3654(Is.No. 21).

Manoharan M. et al., "Cholic Acid–Oligonucliotide Conjugates for Antisense Applications", *Bioorganic Med. Chem. Letts.,* 1994, 4, 1053–1060 (Iss. No. 8).

Manoharan, M. et al., "Chemical Modifications to Improve Uptake and Bioavailability of Antisense Oligonucleotides", *Annals NY Acad. Sciences,* 1992, 660, 306–309.

Manoharan M. et al., "Oligonucleotide Conjugates: Alteration of the Pharmacokinetic Properties of Antisense Agents", *Nucleosides and Nucleotides,* 1995, 14, 969–973(Iss No. 3–5).

Manoharan, M. et al., "Introduction of a Lipophilic Thioether Tether in the Minor Groove of Nucleic Acids for Antisense Applications", *Bioorg. Med. Chem. Letts.,* 1993, 3, 2765–2770 (issue No. 12).

Martin, P., "Ein neuer Zugang zu 2'–O–Alkylribonucleosiden und Eigenschaften deren Oligonucleotide", *Helvetica Chemica Acta,* 1995, 78, 486–504 (English abstract included).

Mertes, M.P. et al., "Synthesis of Carbonate Analogs of Dinucleosides. 3'–Thymidinyl 5'–Thymidinyl Carbonate, 3'–Thymidinyl 5'–(5–Fluoro–2'–deoxyuridinyl) Carbonate, and 3'–(5–Fluoro–2'–deoxyuridinyl) 5'–Thymidinyl Carbonate", *J. Med. Chem.,* 1969, 12, 154–157 (Jan. 1969).

Milligan, J.F. et al., "Current Concepts in Antisense Drug Design," *Journal of Medicinal Chemistry,* 1993, 36(14), 1923–1937 (Jul. 9, 1993).

Mishra, R.K. et al., "Improved leishmanicidal effect of phosphorotioate antisense oligonucleotides by LDL–medicated delivery", *Biochim. Et Biophysica,* 1995, 1264, 229–237.

Monia, B.P. et al., "Evaluation of 2'–Modified Oligonucleotides Containing 2'–Deoxy Gaps as Antisense Inhibitors of Gene Expression", *J. Biol. Chem.,* 1993, 268, 14514–14522(Jul. 5, 1993).

Mungall, W.S. et al., "Carbamate Analogues of Oligonucleotides", *J. Org. Chem.,* 1977, 42, 703–706 (Issue No. 4).

Musicki, B. et al., "Synthesis of Carbohydrate Sulfonates and Sulfonate Esters", *J. Org. Chem.,* 1990, 55, 4231–4233 (Jul. 6, 1990,.Issue No;14).

Oberhauser, B. et al., "Effective incorporation of 2'–O–methyl–oligonucleotides into liposomes and enhanced cell association through modification with thiocholesterol", *Nucl. Acids Res.,* 1992, 20, 533–538 (Issue No. 3).

Polushin, N. N. et al., "Synthesis of Oligonucleotides Containing 2'–Azido–and 2'–Amino–2'–deoxyuridine Using Phosphotriester Chemistry," *Tetrahedron Letts.,* 1996, 37(19), 3227–3230.

Rao, M.V. et al., "Dibenzoyl Tetrasulphide—A Rapid Sulphur Transfer Agent in the Synthesis of Phosphorothioate Analogues of Oligonucleotides", *Tetrahedron Letts.,* 1992, 33, 4839–4842 (Issue No. 33).

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.,* 1991, 56, 4329–4333 (Jun. 21, 1991, Iss. No. 13).

Reynolds, R.C. et al., "Synthesis of Thymidine Dimers Containing Internucleoside Sulfonate and Sulfonamide Linkages", *J. Org. Chem.,* 1992, 57, 2983–2985 (No. 11).

Saison–Behmoaras, T. et al., "Short modified antisense oligonucleotides directed against Ha–ras point mutation induce selective cleavage of the mRNA and inhibit T24 cells proliferation", *EMBO J.,* 1991, 10, 1111–1118 (Issue No. 5).

Searle, M. S. et al., "On the Stability of Nucleic Acids Structures in Solution: Enthalpy–Entropy Compensations, Internal Rotations and Reversibility," *Nucl. Acids Res.,* 1993, 21(9), 2051–2056.

Secrist, J.A. et al., "Synthesis and Biological Activity of 4'–Thionucleosides", 10th International Roundtable: Nucleosides, Nucleotides and their Biological Applications, Sep. 16–20 1992, Abstract 21, Park City, Utah, 40.

Shea, R.G. et al., "Synthesis, hybridization properties and antiviral activity of lipid–oligodeoxynucletide conjugates", *Nucl. Acids Res.,* 1990, 18, 3777–3783 (Iss. No. 13).

Sood, A. et al., "Boron–Containing Nucleic Acids. 2. Synthesis of Oligodeoxynucleoside Boranophosphates", *J. Am. Chem. Soc.,* 1990, 112, 9000–9001.

Stec, W.J. et al., "Bis (O,O–Diisopropoxy Phosphinothioyl) Disulfide—A Highly Efficient Sulfurizing Reagent for Cost–Effective Synthesis of Oligo(Nucleoside Phosphorothioate)s", *Tetrahedron Letts.,* 1993, 34, 5317–5320 (Issue No. 33).

Stein, C.A. et al., "Oligonucleotides as Inhibitors of Gene Expression: A Review", *Cancer Res.,* 1988, 48, 2659–2668 (May 15, 1988).

Stirchak, E.P. et al., "Uncharged Stereoregular Nucleic Acids Analogs. I. Synthesis of a Cytosine–Containing Oligomer with Carbamate Internucleoside Linkages", *J. Org Chem.,* 1987, 52, 4202–4206 (Issue No. 19).

Stirchak, E.P. et al., "Uncharged stereoregular nucleic acids analogs: 2. Morpholino nucleoside oligomer with carbamate internucleoside linkages", *Nucl. Acids Res.,* 1989, 17, 6129–6134 (Issue No. 15).

Svinarchuk, F.P. et al., "Inhibition of HIV proliferation in MT–4 cells by antisense oligonucleotide conjugated to lipophilic groups", *Biochimie,* 1993, 49–54 (vol. 75).

Thomson, J. B. et al., "Synthesis and Properties of Diuridine Phosphate Analogues Containing Thio and Amino Modifications," *J. Org. Chem.,* 1996, 61, 6273–6281 (No. 18).

Uhlmann, E. et al., "Antisense Oligonucleotides: A New Therapeutic Principle", *Chem. Reviews,* 1990, 90, 544–584 (Jun., 1990).

Vasseur, J.J. et al., "Oligonucleosides: Synthesis of a Novel Methylhydroxylamine–linked Nucleoside Dimer and Its Incorporation into Antisense Sequences", *J. Am. Chem. Soc.,* 1992, 114, 4006–4007.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letts.,* 1991, 32, 3005–3008 (Issue No. 26).

Wagner, R. W. et al., "Antisense Gene Inhibition by Oligonucleotides Containing C–5 Propyne Pyrimidines," *Science,* 1993, 260, 1510–1513 (Jun. 4, 1993).

Wang, H. et al., "Solid Phase Synthesis of Neutral Oligonucleotide Analogues", *Tetrahedron Letts.,* 1991, 32, 7385–7388 (Issue No. 50).

Wright, P. et al., "Large Scale Synthesis of Oligonucleotides via phosphoramidite Nucleosides and a High–loaded Polystyrene Support", *Tetrahedron Letts.,* 1993, 34, 3373–3376 (Issue No. 21).

Young, S. L. et al., "Triple Helix Formation Inhibits Transcription Elongation In Vitro," *Proc. Natl. Acad. Sci. USA,* 1991, 88, 10023–10026 (Nov., 1991).

Grotli et al., "2'–O(Carbamoylmethyl)oligonucleotides," *Tetrahedron,* 55(14), 4299–4314 (1999).

Seio et al., "Chemical Synthesis and Properties of Conformationally Fixed Diuridine Monophosphates as Building Blocks of the RNA Turn Motif," *Journal of Organic Chemistry,* 63(5), 1429–1443 (Mar. 6, 1998).

Sekine et al., "Chemical Synthesis and Properties of an Interresidually Cyclized Uridinyl(3'–5')uridine as a Model of tRNA U–Turn Structure Having a Sharp Bend," *Journal of the American Chemical Society,* 116(10), 4469–4470 (May 18, 1994).

Keller et al. (I). "Synthesis and Hybridization Properties of Oligonucleotides Containing 2'–O–Modified Ribonucleotides," *Nucleic Acids Research,* 21(19), 4499–4505 (Sep. 25, 1993).

Keller et al. (II), "51. A General Method for the Synthesis of 2'–O–Modified Ribonucleotides," *Helvetica Chimica Acta,* 76(2), 884–892 (Mar. 24, 1993).

Reddy et al.(III), "Fast Cleavage and Deprotection of Oligonucleotides," *Tetrahedron Letters,* 4311–4314 (Jun. 20, 1994).

| Cmpd # | Bx | X | Y |
|---|---|---|---|
| 5 | 5-methyluracil | 2-cyanoethyl-N,N-diisopropylphosphoramidite | DMT |
| 4b | 5-methyluracil | succinyl linker to CPG | DMT |
| 18 | adenine | H | TBDPS |
| 41 | adenine | H | H |
| 48b | guanine | H | TBDPS |

| Compound # | Bx | E₁ | E₂ |
|---|---|---|---|
| 26 | 5-methyluracil | methyl | methyl |
| 27, 28 | 5-methyluracil | H | polyamine |
| 29 | 5-methyluracil | H | polpeptide |
| 30 | 5-methyluracil | H | linked-cholesterol |
| 31 | 5-methyluracil | H | linked folic acid |
| 43 | 5-methyluracil | H | -CH$_2$CH$_2$-S-CH$_3$ |

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: antisense
      sequence

<400> SEQUENCE: 1
gcgttttttt tttgcg                                                        16

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 2
ctcgtacttt tccggtcc                                                      18

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: antisense
      sequence

```
<400> SEQUENCE: 3
tccaggtgtc cgcatc                                                       16

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: antisense
      sequence

<400> SEQUENCE: 4
tttttttttt tttttttt                                                     19

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: antisense
      sequence

<400> SEQUENCE: 5
tttttttttt tt                                                           12

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: antisense
      sequence

<400> SEQUENCE: 6
ctcgtacttt tccggtcc                                                     18
```

2'-O-ACETAMIDO MODIFIED MONOMERS AND OLIGOMERS

FIELD OF THE INVENTION

The present invention relates to 2'-O-acetamido modified nucleosides and to oligomeric compounds prepared having at least one of these nucleosides. Also included is a process for the deprotection of solid support bound oligomers having at least one nucleoside of the invention. The oligomeric compounds of the present invention are expected to have enhanced nuclease resistance and superior hybridization properties. The oligomeric compounds are useful for investigative and therapeutic purposes.

BACKGROUND OF THE INVENTION

It is well known that most of the bodily states in mammals, including most disease states, are affected by proteins. Classical therapeutic modes have generally focused on interactions with such proteins in an effort to moderate their disease-causing or disease-potentiating functions. Recently, however, attempts have been made to moderate the actual production of such proteins by interactions with molecules that direct their synthesis, such as intracellular RNA. By interfering with the production of proteins, maximum therapeutic effect and minimal side effects may be realized. It is the general object of such therapeutic approaches to interfere with or otherwise modulate gene expression leading to undesired protein formation.

One method for inhibiting specific gene expression is the use of oligonucleotides. Oligonucleotides are now accepted as therapeutic agents with great promise. Oligonucleotides are known to hybridize to single-stranded DNA or RNA molecules. Hybridization is the sequence-specific base pair hydrogen bonding of nucleobases of the oligonucleotide to the nucleobases of the target DNA or RNA molecule. Such nucleobase pairs are said to be complementary to one another. The concept of inhibiting gene expression through the use of sequence-specific binding of oligonucleotides to target RNA sequences, also known as antisense inhibition, has been demonstrated in a variety of systems, including living cells. See, Wagner et al., Science (1993) 260: 1510–1513; Milligan et al., *J. Med. Chem.,* (1993) 36:1923–37; Uhlmann et al., *Chem. Reviews,* (1990) 90:543–584; Stein et al., *Cancer Res.,* (1988) 48:2659–2668.

Events that provide disruption of the nucleic acid function by antisense oligonucleotides (Cohen in *Oligonucleotides: Antisense Inhibitors of Gene Expression,* (1989) CRC Press, Inc., Boca Raton, Fla.) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller and Ts'O, *Anti-Cancer Drug Design,* 1987, 2:117–128) and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Oligonucleotides may also bind to duplex nucleic acids to form triplex complexes in a sequence specific manner via Hoogsteen base pairing (Beal et al., *Science,* (1991) 251:1360–1363; Young et al., *Proc. Natl. Acad. Sci.* (1991) 88:10023–10026). Both antisense and triple helix therapeutic strategies are directed towards nucleic acid sequences that are involved in or responsible for establishing or maintaining disease conditions. Such target nucleic acid sequences may be found in the genomes of pathogenic organisms including bacteria, yeasts, fungi, protozoa, parasites, viruses, or may be endogenous in nature. By hybridizing to and modifying the expression of a gene important for the establishment, maintenance or elimination of a disease condition, the corresponding condition may be cured, prevented or ameliorated.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides may also be of therapeutic value when they bind to non-nucleic acid biomolecules such as intracellular or extracellular polypeptides, proteins, or enzymes. Such oligonucleotides are often referred to as 'aptamers' and they typically bind to and interfere with the function of protein targets (Griffin et al., *Blood,* (1993), 81:3271–3276; Bock et al., *Nature,* (1992) 355: 564–566).

Oligonucleotides and their analogs have been developed and used for diagnostic purposes, therapeutic applications and as research reagents. For use as therapeutics, oligonucleotides must be transported across cell membranes or be taken up by cells, and appropriately hybridize to target DNA or RNA. These critical functions depend on the initial stability of the oligonucleotides toward nuclease degradation. A serious deficiency of unmodified oligonucleotides which affects their hybridization potential with target DNA or RNA for therapeutic purposes is the enzymatic degradation of administered oligonucleotides by a variety of intracellular and extracellular ubiquitous nucleolytic enzymes referred to as nucleases. For oligonucleotides to be useful as therapeutics or diagnostics, the oligonucleotides should demonstrate enhanced binding affinity to complementary target nucleic acids, and preferably be reasonably stable to nucleases and resist degradation. For a non-cellular use such as a research reagent, oligonucleotides need not necessarily possess nuclease stability.

A number of chemical modifications have been introduced into oligonucleotides to increase their binding affinity to target DNA or RNA and increase their resistance to nuclease degradation.

Modifications have been made to the ribose phosphate backbone of oligonucleotides to increase their resistance to nucleases. These modifications include use of linkages such as methyl phosphonates, phosphorothioates and phosphorodithioates, and the use of modified sugar moieties such as 2'-O-alkyl ribose. Other oligonucleotide modifications include those made to modulate uptake and cellular distribution. A number of modifications that dramatically alter the nature of the internucleotide linkage have also been reported in the literature. These include non-phosphorus linkages, peptide nucleic acids (PNA's) and 2'–5' linkages. Another modification to oligonucleotides, usually for diagnostic and research applications, is labeling with non-isotopic labels, e.g., fluorescein, biotin, digoxigenin, alkaline phosphatase, or other reporter molecules.

A variety of modified phosphorus-containing linkages have been studied as replacements for the natural, readily cleaved phosphodiester linkage in oligonucleotides. In general, most of them, such as the phosphorothioate, phosphoramidates, phosphonates and phosphorodithioates all result in oligonucleotides with reduced binding to complementary targets and decreased hybrid stability. In order to make effective therapeutics therefore this binding and hybrid stability of antisense oligonucleotides needs to be improved.

Of the large number of modifications made and studied, few have progressed far enough through discovery and development to deserve clinical evaluation. Reasons underlying this include difficulty of synthesis, poor binding to target nucleic acids, lack of specificity for the target nucleic acid, poor in vitro and in vivo stability to nucleases, and poor pharmacokinetics. Several phosphorothioate oligonucleotides and derivatives are presently being used as antisense agents in human clinical trials for the treatment of various disease states. Approval to use the antisense drug, Fomivirsen, to treat cytomegalovirus (CMV) retinitis in humans was recently granted by both the United States and European regulatory agencies.

The structure and stability of chemically modified nucleic acids is of great importance to the design of antisense oligonucleotides. Over the last ten years, a variety of synthetic modifications have been proposed to increase nuclease resistance, or to enhance the affinity of the antisense strand for its target mRNA (Crooke et al., *Med. Res. Rev.*, 1996, 16, 319–344; De Mesmaeker et al., *Acc. Chem. Res.*, 1995, 28, 366–374). Although a great deal of information has been collected about the types of modifications that improve duplex formation, little is known about the structural basis for the improved affinity observed.

RNA exists in what has been termed "A Form" geometry while DNA exists in "B Form" geometry. In general, RNA:RNA duplexes are more stable, or have higher melting temperatures ($T_m$) than DNA:DNA duplexes (Sanger et al., *Principles of Nucleic Acid Structure*, 1984, Springer-Verlag; New York, N.Y.; Lesnik et al., *Biochemistry*, 1995, 34, 10807–10815; Conte et al., *Nucleic Acids Res.*, 1997, 25, 2627–2634). The increased stability of RNA has been attributed to several structural features, most notably the improved base stacking interactions that result from an A-form geometry (Searle et al., *Nucleic Acids Res.*, 1993, 21, 2051–2056). The presence of the 2' hydroxyl in RNA biases the sugar toward a C3' endo pucker, i.e., also designated as Northern pucker, which causes the duplex to favor the A-form geometry. On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.). In addition, the 2' hydroxyl groups of RNA can form a network of water mediated hydrogen bonds that help stabilize the RNA duplex (Egli et al., *Biochemistry*, 1996, 35, 8489–8494).

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051–2056). The structure of a hybrid duplex is intermediate between A- and B-form geometries, which may result in poor stacking interactions (Lane et al., *Eur. J. Biochem.*, 1993, 215, 297–306; Fedoroff et al., *J. Mol. Biol.*, 1993, 233, 509–523; Gonzalez et al., *Biochemistry*, 1995, 34, 4969–4982; Horton et al., *J. Mol. Biol.*, 1996, 264, 521–533). The stability of a DNA:RNA hybrid is central to antisense therapies as the mechanism requires the binding of a modified DNA strand to a mRNA strand. To effectively inhibit the mRNA, the antisense DNA should have a very high binding affinity with the mRNA. Otherwise the desired interaction between the DNA and target mRNA strand will occur infrequently, thereby decreasing the efficacy of the antisense oligonucleotide.

One synthetic 2'-modification that imparts increased nuclease resistance and a very high binding affinity to nucleotides is the 2'-methoxyethoxy (MOE, 2'—OCH$_2$CH$_2$OCH$_3$) side chain (Baker et al., *J. Biol. Chem.*, 1997, 272, 11944–12000; Freier et al., *Nucleic Acids Res.*, 1997, 25, 4429–4443). One of the immediate advantages of the MOE substitution is the improvement in binding affinity, which is greater than many similar 2' modifications such as O-methyl, O-propyl, and O-aminopropyl (Freier and Altmann, *Nucleic Acids Research*, (1997) 25:4429–4443). Oligonucleotides and oligonucleotide analogs having 2'-O-methoxyethyl-substitutions have also been shown to be antisense inhibitors of gene expression with promising features for in vivo use (Martin, *Helv. Chim. Acta*, 1995, 78, 486–504; Altmann et al., *Chimia*, 1996, 50, 168–176; Altmann et al., *Biochem. Soc. Trans.*, 1996, 24, 630–637; and Altmann et al., *Nucleosides Nucleotides*, 1997, 16, 917–926). Relative to DNA, they display improved RNA affinity and higher nuclease resistance. Chimeric oligonucleotides with 2'-O-methoxyethyl-ribonucleoside wings and a central DNA-phosphorothioate window also have been shown to effectively reduce the growth of tumors in animal models at low doses. MOE substituted oligonucleotides have shown outstanding promise as antisense agents in several disease states. One such MOE-substituted oligonucleotide is currently available for the treatment of CMV retinitis.

A modification that has received limited attention is the 2'-O-acetamido modification in monomers and oligomers. Although not the main focus, a few compounds have been reported in literature and patent publications. Included are 2-aminoanthraquinone, 2'-6-N,N-dimethylaminohexylacetamido, trifluoroacetamidohexyl and monoalkyl groups linked to the nitrogen atom of 2'-O-acetamido groups (Keller et al., *Nucleic Acids Res.*, 1993, 21, 4499–4505; Keller et al., *Helv. Chim. Acta*, 1993, 76, 884–892). Dialkylaminoalkyl, aminoalkyl, and drug substituted and unsubstituted 2'-O-acetamido groups in nucleotides and oligonucleotides have also been reported in U.S. Pat. Nos. 5,466,786, B1 5,466,786 and 5,792,847. The forgoing publications disclose only a few specific 2'-modified monomers and oligomers as their main focus is on other 2'-modifications.

Although the known modifications to oligonucleotides, including the use of the 2'-O-methoxyethyl modification, have contributed to the development of oligonucleotides for various uses, there still exists a need in the art for further modifications that will impart enhanced hybrid binding affinity and/or increased nuclease resistance to oligonucleotides and their analogs.

SUMMARY OF THE INVENTION

In accordance with one embodiment of the present invention there are provided compounds of the formula:

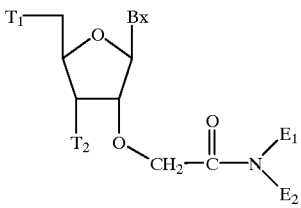

wherein:

Bx is a heterocyclic base moiety;

each $T_1$ and $T_2$ is, independently, OH, a protected hydroxyl;

or one of $T_1$ and $T_2$ is OH or a protected hydroxyl and the other of $T_1$ and $T_2$ is a solid support or an activated phosphorus group;

each $E_1$ and $E_2$ is, independently, $C_1$–$C_{10}$ alkyl;

or each $E_1$ and $E_2$ is, independently, H, —$(CH_2)_m$—S—$R_4$, a polyamine a polypeptide, folic acid moiety or a cholesterol moiety, provided that only one of $E_1$ and $E_2$ is H; and $R_4$ is H, $C_1$–$C_{10}$ alkyl, $C_2$–$C_{10}$ alkenyl, $C_2$–$C_{10}$ alkynyl, $C_6$–$C_{14}$ aryl or a thio protecting group.

In one embodiment both $E_1$ and $E_2$ are $C_1$–$C_{10}$ alkyl. In another embodiment $E_1$ is H and $E_2$ is —$(CH_2)_m$—S—$R_4$. Preferably, $R_4$ is $C_1$–$C_{10}$ alkyl. More preferably, $R_4$ is methyl.

In another embodiment $E_2$ is a polyamine. A preferred polyamine is a spermine or a spermidine. In a further embodiment $E_2$ is a polypeptide. A preferred polypeptide is Lys-Tyr-Lys, Lys-Trp-Lys or Lys-Lys-Lys-Lys. In another embodiment $E_2$ is a folic acid moiety. In a further embodiment $E_2$ is a cholesterol moiety.

In a further embodiment the heterocyclic base moiety is a purine or a pyrimidine. Preferred heterocyclic base moieties include adenine, cytosine, 5-methylcytosine, thymine, uracil, guanine and 2-aminoadenine.

In one preferred embodiment $T_1$ is a protected hydroxyl and $T_2$ is an activated phosphorus group.

In accordance with one embodiment of the present invention there are provided oligomeric compounds having at least one moiety of the formula:

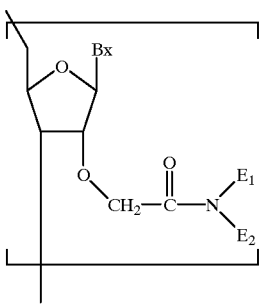

wherein:

Bx is a heterocyclic base moiety;

each $E_1$ and $E_2$ is, independently, $C_1$–$C_{10}$ alkyl;

or each $E_1$ and $E_2$ is, independently, H, —$(CH_2)_m$—S—$R_4$, a polyamine a polypeptide, folic acid moiety optionally bearing a linking group or a cholesterol moiety optionally bearing a linking group, provided that only one of $E_1$ and $E_2$ is H; and $R_4$ is H, $C_1$–$C_{10}$ alkyl, $C_2$–$C_{10}$ alkenyl, $C_2$–$C_{10}$ alkynyl, $C_6$–$C_{14}$ aryl or a thio protecting group.

In one embodiment of the present invention both $E_1$ and $E_2$ are $C_1$–$C_{10}$ alkyl. In another embodiment $E_1$ is H and $E_2$ is —$(CH_2)_m$—S—$R_4$. Preferably $R_4$ is $C_1$–$C_{10}$ alkyl. More preferably $R_4$ is methyl.

In another embodiment $E_2$ is a polyamine. A preferred polyamine is a spermine or a spermidine. In a further embodiment $E_2$ is a polypeptide. A preferred polypeptide is Lys-Tyr-Lys, Lys-Trp-Lys and Lys-Lys-Lys-Lys. In another embodiment $E_2$ is a folic acid moiety which may optionally bear a linking group. In a further embodiment $E_2$ is a cholesterol moiety which may optionally bear a linking group.

In one embodiment the heterocyclic base moiety is a purine or a pyrimidine. It is preferred that the heterocyclic base moiety be adenine, cytosine, 5-methylcytosine, thymine, uracil, guanine or 2-aminoadenine.

In one preferred embodiment $T_1$ is a protected hydroxyl and $T_2$ is an activated phosphorus group.

In one embodiment the oligomeric compound comprises from about 5 to about 50 nucleosides. In a preferred embodiment the oligomeric compound comprises from about 8 to about 30 nucleosides and in a more preferred embodiment the oligomeric compound comprises from about 15 to about 25 nucleosides.

The present invention also provides a process for preparing a deprotected oligomeric compound comprising the steps of:

(a) selecting a solid support bound oligomeric compound having at least one moiety of the formula:

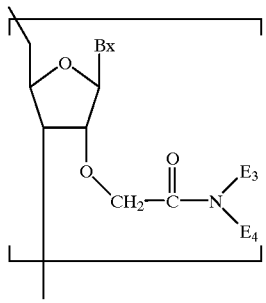

wherein:

Bx is an optionally protected heterocyclic base moiety;

each $E_3$ and $E_4$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)(R_4)$, guanidino or acyl where said acyl is an acid, amide or an ester;

each $R_3$ and $R_4$ is, independently, H, $C_1$–$C_{10}$ alkyl, $C_2$–$C_{10}$ alkenyl, $C_2$–$C_{10}$ alkynyl, $C_6$–$C_{14}$ aryl, a nitrogen protecting group, a thio protecting group, or $R_3$ and $R_4$, together, are a nitrogen protecting group;

or $R_3$ and $R_4$ are joined in a ring structure that optionally includes an additional heteroatom selected from N and O;

(b) contacting said solid support bound oligomeric compound with a solution of ammonium hydroxide at ambient temperature to give a basic mixture; and (c) adding a solution of methylamine to said basic mixture at ambient temperature to provide the deprotected oligomeric compound.

In one embodiment the solid support bound oligomeric compound is contacted with ammonium hydroxide from about one hour to about 3 hours, with about 2 hours being preferred.

In another embodiment the concentration of ammonium hydroxide in said solution is from about 20% to saturated, with a saturated solution being preferred.

In a further embodiment the ambient temperature is from about 15° C. to about 30° C., with 20° C. to about 25° C. being preferred.

In one embodiment the solution of methylamine is from about 30% to about 50% methylamine in water, with 40% being preferred.

In another embodiment step (c) is performed over a period of time from about 10 hours to about 30 hours, with 26 hours being preferred.

In a preferred embodiment the solid support is CPG.

DETAILED DESCRIPTION OF PREFERRED EMBODIMENTS

Figure 1:
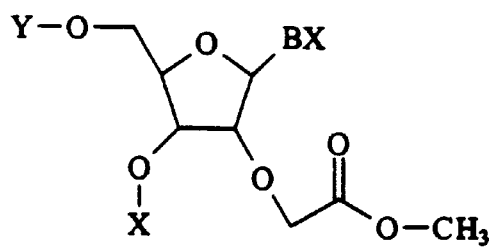
FIG. 1 shows certain intermediates of the invention.
Figure 2:
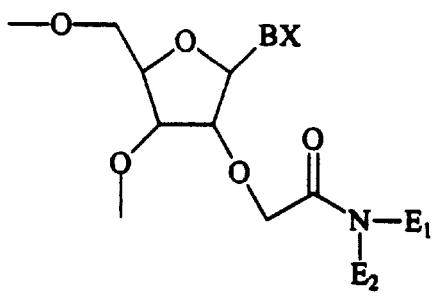
FIG. 2 shows certain 2'-O-groups of the invention.

The present invention provides 2'-O-acetamido modified nucleoside monomers, oligomeric compounds prepared therefrom and a novel process for the deprotection of the oligomeric compounds from a solid support. The 2'-O-acetamido modified oligomeric compounds of the invention are expected to have improved hybridization and nuclease resistance properties.

The present invention presents modified nucleosidic monomers and oligomers prepared therefrom. The monomers each comprise a nucleoside having at least one modification which is preferably at the 2'-position, but may be at a 3' or 5'-position of the sugar, or at a heterocyclic base position. More than one position can be modified in either the nucleosidic monomers or oligomers of the present invention. The oligomeric compounds of the invention are useful for identification or quantification of an RNA or DNA or for modulating the activity of an RNA or DNA molecule. The oligomeric compounds having a modified nucleosidic monomer therein are preferably prepared to be specifically hybridizable with a preselected nucleotide sequence of a single-stranded or double-stranded target DNA or RNA molecule. It is generally desirable to select a sequence of DNA or RNA which is involved in the production of a protein whose synthesis is ultimately to be modulated or inhibited in its entirety or to select a sequence of RNA or DNA whose presence, absence or specific amount is to be determined in a diagnostic test.

In one aspect of the present invention the nucleosidic monomers of the invention are prepared having at least one 2'-O-acetamido modification having formula I:

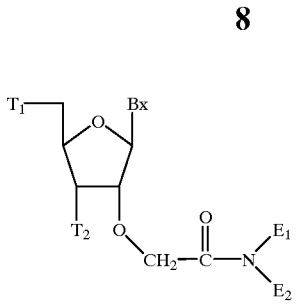

wherein:
Bx is a heterocyclic base moiety;
each $T_1$ and $T_2$ is, independently, OH, a protected hydroxyl;
or one of $T_1$ and $T_2$ is OH or a protected hydroxyl and the other of $T_1$ and $T_2$ is a solid support or an activated phosphorus group;
each $E_1$ and $E_2$ is, independently, $C_1$–$C_{10}$ alkyl;
or each $E_1$ and $E_2$ is, independently, H, —$(CH_2)_m$—S—$R_4$, a polyamine, a polypeptide, a folic acid moiety optionally bearing a linking group or a cholesterol moiety optionally bearing a linking group, provided that only one of $E_1$ and $E_2$ is H; and
$R_4$ is H, $C_1$–$C_{10}$ alkyl, $C_2$–$C_{10}$ alkenyl, $C_2$–$C_{10}$ alkynyl, $C_6$–$C_{14}$ aryl or a thio protecting group.

It is preferred that the oligomeric compounds of the invention be adapted to be specifically hybridizable with the nucleotide sequence of the target RNA or DNA selected for modulation. Oligomeric compounds particularly suited for the practice of one or more embodiments of the present invention comprise 2'-sugar modified nucleosides wherein the modification is an acetamido moiety. For example, the oligomeric compounds are modified to contain substitutions including but not limited incorporation of one or more nucleoside units modified as shown in formula I above.

The present invention also discloses a novel process for deprotecting oligomeric compounds incorporating at least one modified nucleoside of formula I above from a solid support. The process has the advantage of maintaining the integrity of 2'-O-acetamido modified nucleosides incorporated in oligomeric compounds during deprotection/cleavage from solid support. The process is as effective yet milder than standard processes routinely used employing elevated temperatures for longer time periods. The process also removes heterocyclic base protecting groups simultaneously with the cleavage of the oligomeric compound from the solid support. The process is applicable to deprotecting oligomeric compounds in addition to those that are 2'-O-acetamido modified. However the present process has an extra step and therefor would be especially useful for deprotecting oligomeric compounds that are labile under standard deprotection processes.

An optionally protected solid support bound oligomeric compound is treated with a solution of ammonium hydroxide for about 2 hours at ambient temperatures (from about 15° C. to about 30° C.). To the resulting solution is added a solution of methylamine (commercially available 40% aqueous). Other concentrations of methylamine from about 25% to about 50% are amenable to the present invention. Methylamine solutions of these concentrations need to be prepared, which is not required with the commercially available reagent. The methylamine solution is added until it comprises about 10% of the total volume of the mixture. This mixture is allowed to stand at ambient temperature for about 10 to about 30 hours. At about 26 hours most deprotection reactions were complete.

The nucleosidic monomers of the present invention can include appropriate activated phosphorus groups such as activated phosphate groups and activated phosphite groups. As used herein, the terms activated phosphate and activated phosphite groups refer to activated monomers or oligomers that react with a hydroxyl group of another monomeric or oligomeric compound to form a phosphorus-containing internucleotide linkage. Such activated phosphorus groups contain activated phosphorus atoms in $P^{III}$ or $P^V$ valency states. Such activated phosphorus atoms are known in the art and include, but are not limited to, phosphoramidite, H-phosphonate and phosphate triesters. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in preferred embodiments, phosphodiester or phosphorothioate internucleotide linkages. Additional activated phosphates and phosphates are disclosed in Tetrahedron Report Number 309 (Beaucage and Iyer, *Tetrahedron*, 1992, 48, 2223–2311).

The oligomeric compounds of the invention are conveniently synthesized using solid phase synthesis of known methodology, and are preferably designed to be complementary to or specifically hybridizable with a preselected nucleotide sequence of the target RNA or DNA. Standard solution phase and solid phase methods for the synthesis of oligomeric compounds are well known to those skilled in the art. These methods are constantly being improved in ways that reduce the time and cost required to synthesize these complicated compounds. Representative solution phase techniques are described in U.S. Pat. No. 5,210,264, issued May 11, 1993 and commonly assigned with this invention. Representative solid phase techniques employed for the synthesis of oligomeric compounds utilizing standard phosphoramidite chemistries are described in Protocols For Oligonucleotides And Analogs, S. Agrawal, ed., Humana Press, Totowa, N.J., 1993.

The oligomeric compounds of the invention also include those that comprise nucleosides connected by charged linkages and whose sequences are divided into at least two regions. In some preferred embodiments, the first region includes 2'-O-acetamido substituted-nucleosides linked by a first type of linkage, and the second region includes nucleosides linked by a second type of linkage. In other preferred embodiments, the oligomers of the present invention further include a third region comprised of nucleosides as are used in the first region, with the second region positioned between the first and the third regions. Such oligomeric compounds are known as "chimeras," "chimeric," or "gapped" oligomers (See, e.g., U.S. Pat. No. 5,623,065, issued Apr. 22, 1997, the contents of which are incorporated herein by reference).

Gapmer technology has been developed to incorporate modifications at the ends ("wings") of oligomeric compounds, leaving a phosphorothioate gap in the middle for RNase H activation (Cook, P. D., *Anti-Cancer Drug Des.*, 1991, 6, 585–607; Monia et al., *J. Biol. Chem.*, 1993, 268, 14514–14522). In a recent report, the activities of a series of uniformly 2'-O modified 20 mer RNase H-independent oligonucleotides that were antisense to the 5'-cap region of human ICAM-1 transcript in HUVEC cells, were compared to the parent 2'-deoxy phosphorothioate oligonucleotide (Baker et al., *J. Bio. Chem.*, 1997, 272, 11994–12000). The 2'-MOE/P=O oligomer demonstrated the greatest activity with a $IC_{50}$ of 2.1 nM ($T_m$=87.1° C.), while the parent P=S oligonucleotide analog had an $IC_{50}$ of 6.5 nM ($T_m$=79.2° C.). Correlation of activity with binding affinity is not always observed as the 2'-F/P=S ($T_m$=87.9° C.) was less active than the 2'-MOE/P=S ($T_m$=79.2° C.) by four fold. The RNase H competent 2'-deoxy P=S parent oligonucleotide exhibited an $IC_{50}$=41 nM.

In the context of this invention, the terms "oligomer" and "oligomeric compound" refer to a plurality of naturally-occurring or non-naturally-occurring nucleosides joined together in a specific sequence. The terms "oligomer" and "oligomeric compound" include oligonucleotides, oligonucleotide analogs, oligonucleosides and chimeric oligomeric compounds where there are more than one type of internucleoside linkages dividing the oligomeric compound into regions. Whereas the term "oligonucleotide" has a well defined meaning in the art, the term "oligomeric compound" or "oligomer" is intended to be broader, inclusive of oligomers having all manner of modifications known in the art. In some preferred embodiments, each of the oligomeric compounds of the invention have at least one modified nucleoside where the modification is an acetamido compound of the invention.

A heterocyclic base moiety (often referred to in the art simply as a "base") amenable to the present invention includes both naturally and non-naturally occurring nucleobases. This heterocyclic base moiety further may be protected wherein one or more functionalities of the base bears a protecting group. As used herein, "unmodified" or "natural" nucleobases include the purine bases adenine and guanine, and the pyrimidine bases thymine, cytosine and uracil. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993.

Certain nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of modified nucleobases include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587, 469; 5,594,121, 5,596,091; 5,614,617; 5,750,692; and 5,681,941, certain of which are commonly owned, and each of which is herein incorporated by reference.

The preferred sugar moieties are deoxyribose or ribose. However, other sugar substitutes known in the art are also amenable to the present invention.

As used herein, the term "sugar substituent group" refers to groups that are attached to sugar moieties of nucleosides that comprise compounds or oligomers of the invention. Sugar substituent groups are covalently attached at sugar 2', 3' and 5'-positions. In some preferred embodiments, the sugar substituent group has an oxygen atom bound directly to the 2', 3' and/or 5'-carbon atom of the sugar. Preferably, sugar substituent groups are attached at 2'-positions although sugar substituent groups may also be located at 3' and 5' positions.

Sugar substituent groups amenable to the present invention include fluoro, O-alkyl, O-alkylamino, O-alkylalkoxy, protected O-alkylamino, O-alkylaminoalkyl, O-alkyl imidazole, and polyethers of the formula $(O-alkyl)_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional sugar substituent groups amenable to the present invention include —SR and —NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230.

Further representative sugar substituent groups amenable to the present invention include those having one of formula II or III:

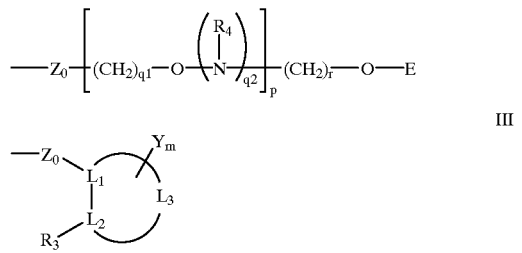

wherein:

Z$_0$ is O, S or NH;

E is $C_1$–$C_{10}$ alkyl, $N(R_4)(R_5)$ or $N=C(R_4)(R_5)$;

each R$_4$ and R$_5$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is OR$_6$, SR$_6$, NH$_3^+$, N(R$_6$) (R$_7$), guanidino or acyl where said acyl is an acid amide or an ester;

or R$_4$ and R$_5$, together, are a nitrogen protecting group or are joined in a ring structure that optionally includes an additional heteroatom selected from N and O; and each R$_6$ and R$_7$ is, independently, H, $C_1$–$C_{10}$ alkyl, a nitrogen protecting group, or R$_3$ and R$_4$, together, are a nitrogen protecting group;

or R$_6$ and R$_7$ are joined in a ring structure that optionally includes an additional heteroatom selected from N and O;

R$_3$ is OX, SX, or $N(X)_2$;

each X is, independently, H, $C_1$–$C_8$ alkyl, $C_1$–$C_8$ haloalkyl, C(=NH)N(H)Z, C(=O)N(H)Z or OC(=O)N(H)Z;

Z is H or $C_1$–$C_8$ alkyl;

L$_1$, L$_2$ and L$_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_4)(R_5)OR_4$, halo, SR$_4$ or CN;

each q$_1$ is, independently, an integer from 2 to 10;

each q$_2$ is, independently, 0 or 1;

p is an integer from 1 to 10; and r is an integer from 1 to 10; provided that when p is 0, r is greater than 1.

Representative 2'-O-sugar substituents of formula II are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic 2'-O-sugar substituents of formula III are disclosed in U.S. patent application Ser. No. 09/123, 108, filed Jul. 27, 1998, entitled "RNA Targeted 2'-Modified Oligonucleotides that are Conformationally Preorganized," hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10.

Some preferred oligomeric compounds of the invention contain, in addition to a 2'-O-acetamido modified nucleoside, at least one nucleoside having one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O-$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or in 2'-5' linked oligomers and the 5' position of 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,859,221; and 5,700,920, certain of which are commonly owned, and each of which is herein incorporated by reference.

Sugars having O-substitutions on the ribosyl ring are also amenable to the present invention. Representative substitutions for ring C include, but are not limited to, S, $CH_2$, CHF, and $CF_2$. See, e.g., Secrist et al., *Abstract* 21, *Program & Abstracts, Tenth International Roundtable, Nucleosides, Nucleotides and their Biological Applications*, Park City, Utah, Sep. 16–20, 1992.

Heterocyclic ring structures of the present invention can be fully saturated, partially saturated, unsaturated or with a polycyclic heterocyclic ring each of the rings may be in any of the available states of saturation. Heterocyclic ring structures of the present invention also include heteroaryl which includes fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

The present invention provides oligomeric compounds comprising a plurality of linked nucleosides wherein the preferred internucleoside linkage is a 3',5'-linkage. Alternatively, 2',5'-linkages can be used (as described in U.S. application Ser. No. 09/115,043, filed Jul. 14, 1998). A 2',5'-linkage is one that covalently connects the 2'-position of the sugar portion of one nucleotide subunit with the 5'-position of the sugar portion of an adjacent nucleotide subunit.

The oligonucleotides of the present invention preferably are about 5 to about 50 bases in length. Preferably, oligonucleotides of the invention have from 8 to about 30 bases, and more preferably from about 15 to about 25 bases.

In one preferred embodiment of the invention blocked/protected and appropriately activated nucleosidic monomers are incorporated into oligomeric compounds in the standard manner for incorporation of a normal blocked and activated standard nucleotide. For example, a DMT phosphoramidite nucleosidic monomer is selected that has a 2'-O-acetamido moiety that can include protection of functional groups. The nucleosidic monomer is added to the growing oligomeric compound by treating with the normal activating agents, as is known is the art, to react the phosphoramidite moiety with the growing oligomeric compound. This may be followed by removal of the DMT group in the standard manner, as is known in the art, and continuation of elongation of the oligomeric compound with normal nucleotide amidite units as is standard in the art. Alternatively, the phosphoramidite can be intended to be the terminus of the oligomeric compound in which case it may be purified with the DMT group on or off following cleavage from the solid support. There are a plurality of alternative methods for preparing oligomeric compounds of the invention that are well known in the art. The phosphoramidite method is meant as illustrative of one of these methods.

In the context of this specification, alkyl (generally $C_1$–$C_{10}$), alkenyl (generally $C_2$–$C_{10}$), and alkynyl (generally $C_2$–$C_1$) groups include but are not limited to substituted and unsubstituted straight chain, branch chain, and alicyclic hydrocarbons, including generally $C_1$–$C_{20}$ alkyl groups, and also including other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyl-octyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl compound, which has further straight or branched chains attached to the carbon atoms of the straight chain. A cyclic compound, as used herein, refers to closed chain compounds, i.e. a ring of carbon atoms, such as an alicyclic or aromatic compound. The straight, branched, or cyclic compounds may be internally interrupted, as in alkoxy or heterocyclic compounds. In the context of this invention, internally interrupted means that the carbon chains may be interrupted with heteroatoms such as O, N, or S. However, if desired, the carbon chain may have no heteroatoms.

As used herein, "polyamine" refers to a moiety containing a plurality of amine or substituted amine functionalities. Polyamines according to the present invention have at least two amine functionalities. "Polypeptide" refers to a polymer comprising a plurality of amino acids linked by peptide linkages, and includes dipeptides and tripeptides. The amino acids may be naturally-occurring or non-naturally-occurring amino acids. Polypeptides according to the present invention comprise at least two amino acids.

In certain preferred embodiments of the present invention, oligomeric compounds are linked via phosphorus linkages. Preferred phosphorus linkages include phosphodiester, phosphorothioate and phosphorodithioate linkages. In one preferred embodiment of this invention, nuclease resistance is conferred on the oligonucleotides by utilizing phosphorothioate internucleoside linkages.

As used herein, the term oligonucleoside includes oligomers or polymers containing two or more nucleoside subunits having a non-phosphorous linking moiety. Oligonucleosides according to the invention have monomeric subunits or nucleosides having a ribofuranose moiety attached to a heterocyclic base moiety through a glycosyl bond.

Oligonucleotides and oligonucleosides can be joined to give a chimeric oligomeric compound. In addition to the naturally-occurring phosphodiester linking group, phosphorus and non-phosphorus containing linking groups that can be used to prepare oligonucleotides, oligonucleosides and oligomeric chimeric compounds (oligomeric compounds) of the invention are well documented in the prior art and include without limitation the following:

phosphorus containing linkages
  phosphorodithioate (—O—P(S)(S)—O—);
  phosphorothioate (—O—P(S)(O)—O—);
  phosphoramidate (—O—P(O)(NJ)—O—);
  phosphonate (—O—P(J)(O)—O—);
  phosphotriesters (—O—P(O J)(O)—O—);
  phophosphoramidate (—O—P(O)(NJ)—S—);
  thionoalkylphosphonate (—O—P(S)(J)—O—);
  thionoalkylphosphotriester (—O—P(O)(OJ)—S—);
  boranophosphate (—$R^5$—P(O)(O)—J—);
non-phosphorus containing linkages
  thiodiester (—O—C(O)—S—);
  thionocarbamate (—O—C(O)(NJ)—S—);
  siloxane (—O—Si(J)$_2$—O—);
  carbamate (—O—C(O)—NH— and —NH—C(O)—O—)
  sulfamate (—O—S(O)(O)—N— and —N—S(O)(O)—N—;
  morpholino sulfamide (—O—S(O) (N(morpholino)—);
  sulfonamide (—O—SO$_2$—NH—);
  sulfide (—CH$_2$—S—CH$_2$—);
  sulfonate (—O—SO$_2$—CH$_2$—);
  N,N'-dimethylhydrazine (—CH$_2$—N(CH$_3$)—N(CH$_3$)—);
  thioformacetal (—S—CH$_2$—O—);
  formacetal (—O—CH$_2$—O—);
  thioketal (—S—C(J)$_2$—O—); and
  ketal (—O—C(J)$_2$—O—);
  amine (—NH—CH$_2$—CH$_2$—)
  hydroxylamine (—CH$_2$—N (J) —O—)
  hydroxylimine (—CH=N—O—); and
  hydrazinyl (—CH$_2$—N(H)—N(H)—).

"J" denotes a substituent group which is commonly hydrogen or an alkyl group, but which can be a more complicated group that varies from one type of linkage to another.

In addition to linking groups as described above that involve the modification or substitution of one or more of the —O—P(O)$_2$—O—atoms of a naturally occurring linkage, included within the scope of the present invention are linking groups that include modification of the 5'-methylene group as well as one or more of the atoms of the naturally occurring linkage. Linking groups (or linkages) of this type are well documented in the literature and include without limitation the following:

amides (—CH$_2$—CH$_2$—N(H)—C(O) ) and —CH$_2$—O—N=CH—; and
  alkylphosphorus (—C(J)$_2$—P(=O)(OJ)—C(J)$_2$—C(J)$_2$—), wherein J is as described above.

Synthetic schemes for the synthesis of the substitute internucleoside linkages described above are disclosed in: WO 91/08213; WO 90/15065; WO 91/15500; WO 92/20822; WO 92/20823; WO 91/15500; WO 89/12060; EP 216860; U.S. Ser. Nos. 92/04294; 90/03138; 91/06855; 92/03385; 91/03680; 07/990,848; 07/892,902; 07/806,710; 07/763,130; 07/690,786; U.S. Pat. Nos. 5,466,677; 5,034,506; 5,124,047; 5,278,302; 5,321,131; 5,519,126; 4,469,863; 5,455,233; 5,214,134; 5,470,967; 5,434,257; Stirchak, E. P., et al., *Nucleic Acid Res.,* 1989, 17, 6129–6141; Hewitt, J. M., et al., 1992, 11, 1661–1666; Sood, A., et al., *J. Am. Chem. Soc.,* 1990, 112, 9000–9001; Vaseur, J. J. et al., *J. Amer. Chem. Soc.,* 1992, 114, 4006–4007; Musichi, B., et al., *J. Org. Chem.,* 1990, 55, 4231–4233; Reynolds, R. C., et al., *J. Org. Chem.,* 1992, 57, 2983–2985; Mertes, M. P., et al., *J. Med. Chem.,* 1969, 12, 154–157; Mungall, W. S., et al., *J. Org. Chem.,* 1977, 42, 703–706; Stirchak, E. P., et al., *J. Org. Chem.,* 1987, 52, 4202–4206; Coull, J. M., et al., *Tet. Lett.,* 1987, 28, 745; and Wang, H., et al., *Tet. Lett.,* 1991, 32, 7385–7388.

Other modifications can be made to the sugar, to the base, or to the phosphate group of the nucleoside. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218, 105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, 5,587,469, all assigned to the assignee of this application. The disclosures of each of the above referenced United States patents are herein incorporated by reference.

The attachment of conjugate groups to oligonucleotides and analogs thereof is well documented in the prior art. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. Pat. No. 5,578,718, issued Jul. 1, 1997, and U.S. Pat. No. 5,218,105. Each of the foregoing is commonly assigned with this application. The entire disclosure of each United States patent is incorporated herein by reference.

Preferred conjugate groups amenable to the present invention include lipid moieties such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylamino-carbonyl-oxycholesterol moiety (Crooke et al., *J. Pharmacol. Exp. Ther.,* 1996, 277, 923).

Other groups for modifying antisense properties include RNA cleaving complexes, pyrenes, metal chelators, porphyrins, alkylators, hybrid intercalator/ligands and photo-crosslinking agents. RNA cleavers include o-phenanthroline/Cu complexes and Ru(bipyridine)$_3^{2+}$ complexes. The Ru(bpy)$_3^{2+}$ complexes interact with nucleic acids and cleave nucleic acids photochemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that could be conjugated using the similar protocols.

Hybrid intercalator/ligands include the photonuclease/intercalator ligand 6-[[[9-[[6-(4-nitro-benzamido)hexyl]amino]acridin-4-yl]carbonyl]amino]hexanoyl-pentafluorophenyl ester. This compound has two noteworthy features: an acridine moiety that is an intercalator and a p-nitro benzamido group that is a photonuclease.

Photo-crosslinking agents include aryl azides such as, for example, N-hydroxysucciniimidyl-4-azidobenzoate (HSAB) and N-succinimidyl-6(-4'-azido-2'-nitrophenyl-amino)hexanoate (SANPAH). Aryl azides conjugated to oligonucleotides effect crosslinking with nucleic acids and proteins upon irradiation, They also crosslink with carrier proteins (such as KLH or BSA), raising antibody against the oligonucleotides.

Vitamins according to the invention generally can be classified as water soluble or lipid soluble. Water soluble vitamins include thiamine, riboflavin, nicotinic acid or niacin, the vitamin $B_6$ pyridoxal group, pantothenic acid, biotin, folic acid, the $B_{12}$ cobamide coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), retinol-binding protein (RBP), and cellular retinol-binding protein (CRBP). These proteins, which have been found in various parts of the human body, have molecular weights of approximately 15 kD. They have specific interactions with compounds of vitamin-A family, especially, retinoic acid and retinol.

In the context of this invention, "hybridization" shall mean hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, also refers to sequence complementarity between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity such that stable and specific binding occurs between the oligonucleotide and the DNA or RNA target. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

Cleavage of oligonucleotides by nucleolytic enzymes requires the formation of an enzyme-substrate complex, or in particular, a nuclease-oligonucleotide complex. The nuclease enzymes will generally require specific binding sites located on the oligonucleotides for appropriate attachment. If the oligonucleotide binding sites are removed or blocked, such that nucleases are unable to attach to the oligonucleotides, the oligonucleotides will be nuclease resistant. In the case of restriction endonucleases that cleave sequence-specific palindromic double-stranded DNA, certain binding sites such as the ring nitrogen in the 3- and 7-positions of heterocyclic base moieties have been identified as required binding sites. Removal of one or more of these sites or sterically blocking approach of the nuclease to these particular positions within the oligonucleotide has provided various levels of resistance to specific nucleases.

This invention provides oligomeric compounds that are expected to possess superior hybridization properties. Structure-activity relationship studies have revealed that an increase in binding ($T_m$) of certain 2'-sugar modified oligonucleotides to an RNA target (complement) correlates with an increased "A" type conformation of the heteroduplex.

It is known from X-ray diffraction analysis of nucleic acid fibers (Arnott and Hukins, *Biochem. Biophys. Res. Comm.,* 1970, 47, 1504) and analysis of crystals of double-stranded nucleic acids that DNA takes a "B" form structure and RNA takes the more rigid "A" form structure. The difference between the sugar puckering (C2' endo for "B" form DNA and C3' endo for "A" form RNA) of the nucleosides of DNA and RNA is the major conformational difference between double-stranded nucleic acids.

The primary contributor to the conformation of the pentofuranosyl moiety is the nature of the substituent at the 2'-position. Thus, the population of the C3'-endo form increases with respect to the C2'-endo form as the electronegativity of the 2'-substituent increases. For example, among 2'-deoxy-2'-haloadenosines, the 2'-fluoro derivative exhibits the largest population (65%) of the C3'-endo form, and the 2'-iodo exhibits the lowest population (7%). Those of adenosine (2'—OH) and deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoroadenosine) is further correlated to the stabilization of the stacked conformation. Research indicates that dinucleoside phosphates have a stacked conformation with a geometry similar to that of A—A but with a greater extent of base-base overlapping than A—A. It is assumed that the highly polar nature of the C2'-F bond and the extreme preference for C3'-endo puckering may stabilize the stacked conformation in an "A" structure.

Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an "A" form duplex than a "B" form duplex.

Thus, a 2'-substituent on the 3'-nucleotidyl unit of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

Studies with a 2'-OMe modification of 2'-deoxy guanosine, cytidine, and uridine dinucleoside phosphates exhibit enhanced stacking effects with respect to the corresponding unmethylated species (2'—OH). In this case, it is believed that the hydrophobic attractive forces of the methyl group tend to overcome the destabilizing effects of its steric bulk.

Melting temperatures (complementary binding) are increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

While not wishing to be bound by any specific theory, the design of acetamido-modified oligomeric compounds is focused on a number of factors that include: an electronegative atom at the 2'-connecting site, which is believed to be necessary for $C_3$,-endo conformation via 04,-02, gauche effect (increase in binding affinity) and gauche effect of the 2'-substituent —O—$CH_2$—C(O)—N(—)—(increase in binding affinity/nuclease resistance). The expected structure is depicted below for one monomer.

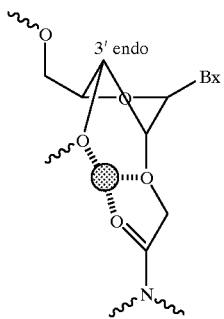

Compounds of the invention can be utilized as diagnostics, therapeutics and as research reagents and in kits. They can be utilized in pharmaceutical compositions by adding an effective amount of an oligomeric compound of the invention to a suitable pharmaceutically acceptable diluent or carrier. They further can be used for treating organisms having a disease characterized by the undesired production of a protein. The organism can be contacted with an oligomeric compound of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 μg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with other traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

The present invention can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include both the eradication of a disease state, killing of an organism, e.g. bacterial, protozoan or other infection, or control of aberrant or undesirable cellular growth or expression.

The current method of choice for the preparation of naturally occurring oligonucleotides as well as oligomeric compounds of the present invention, such as phosphorothioates, is via solid-phase synthesis using a polymer support (a solid support) such as controlled pore glass (CPG); oxalyl-controlled pore glass (see, e.g., Alul, et al., *Nucleic Acids Research* 1991, 19, 1527); TENTAGEL Support, (see, e.g., Wright, et al., *Tetrahedron Letters* 1993, 34, 3373); or POROS, a polystyrene resin available from Perceptive Biosystems. Equipment for such synthesis is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), *Oligonucleotides and Analogues, a Practical Approach*, Oxford University Press, New York (1991).

Solid-phase synthesis relies on sequential addition of nucleotides to one end of a growing oligonucleotide chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Solid supports according to the invention include controlled pore glass (CPG), oxalyl-controlled pore glass (see, e.g., Alul, et al., Nucleic Acids Research 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

2'-Substituted oligonucleotides were synthesized by standard solid phase nucleic acid synthesis using an automated synthesizer such as Model 380B (Perkin Elmer/Applied Biosystems) or MilliGen/Biosearch 7500 or 8800. Triester, phosphoramidite, or hydrogen phosphonate coupling chemistries (Oligonucleotides: *Antisense Inhibitors of Gene Expression*. M. Caruthers, p. 7, J. S. Cohen (Ed.), CRC Press, Boca Raton, Fla., 1989) are used with these synthesizers to provide the desired oligonucleotides. The Beaucage reagent (*J. Amer. Chem. Soc.,* 1990, 112, 1253) or elemental sulfur (Beaucage et al., *Tet. Lett.,* 1981, 22, 1859) is used with phosphoramidite or hydrogen phosphonate chemistries to provide 2'-substituted phosphorothioate oligonucleotides.

Useful sulfurizing agents include Beaucage reagent described in, for example, Iyer et al., *J Am Chem Soc,* 112, 1253–1254 (1990); and Iyer et al., *J Org Chem,* 55, 4693–4699 (1990); tetraethyl-thiuram disulfide as described in Vu et al., *Tetrahedron Lett,* 32, 3005–3007 (1991); dibenzoyl tetrasulfide as described in Rao et al., *Tetrahedron Lett,* 33, 4839–4842 (1992); di(phenylacetyl)disulfide, as described in Kamer et al., *Tetrahedron Lett,* 30, 6757–6760 (1989); Bis(O,O-diisopropoxy phosphinothioyl)disulfide, Stec., *Tetrahedron Letters,* 1993, 34, 5317–5320; sulfur; and sulfur in combination with ligands like triaryl, trialkyl or triaralkyl or trialkaryl phosphines. Useful oxidizing agents, in addition to those set out above, include iodine/tetrahydrofuran/water/pyridine; hydrogen peroxide/water; tert-butyl hydroperoxide; or a peracid like m-chloroperbenzoic acid. In the case of sulfurization, the reaction is performed under anhydrous conditions with the exclusion of air, in particular oxygen; whereas, in the case of oxidation the reaction can be performed under aqueous conditions.

The requisite 2'-substituted nucleosides (A, G, C, T(U), and other nucleosides having modified nucleobases and or additional sugar modifications) are prepared, utilizing procedures as described below.

During the synthesis of nucleoside monomers and oligomeric compounds of the invention, chemical protecting groups can be used to facilitate conversion of one or more functional groups while other functional groups are rendered inactive. A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC, benzoyl or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX) groups. Chemical functional groups can also be "blocked" by including them in a precursor form. Thus, an azido group can be used considered as a "blocked" form of an amine since the azido group is easily converted to the amine. Representative protecting groups utilized in oligonucleotide synthesis are discussed in Agrawal et al., *Protocols for Oligonucleotide Conjugates,* Eds, Humana Press; New Jersey, 1994; Vol. 26 pp. 1–72.

Among other uses, the oligomeric compounds of the invention are useful in a ras-luciferase fusion system using ras-luciferase transactivation. As described in International Publication Number WO 92/22651, published Dec. 23, 1992 and U.S. Pat. Nos. 5,582,972 and 5,582,986, commonly assigned with this application, the entire contents of which United States patent are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon-12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

In addition to modulation of the ras gene, the oligomeric compounds of the present invention that are specifically hybridizable with other nucleic acids can be used to modulate the expression of such other nucleic acids. Examples include the raf gene, a naturally present cellular gene which occasionally converts to an activated form that has been implicated in abnormal cell proliferation and tumor formation. Other examples include those relating to protein kinase C (PKC) that have been found to modulate the expression of PKC, those related to cell adhesion molecules such as ICAM, those related to multi-drug resistance associated protein, and viral genomic nucleic acids include HIV, herpesviruses, Epstein-Barr virus, cytomegalovirus, papillomavirus, hepatitis C virus and influenza virus (see, U.S. Pat. Nos. 5,166,195, 5,242,906, 5,248,670, 5,442,049, 5,457,189, 5,510,476, 5,510,239, 5,514,577, 5,514,786, 5,514,788, 5,523,389, 5,530,389, 5,563,255, 5,576,302, 5,576,902, 5,576,208, 5,580,767, 5,582,972, 5,582,986, 5,591,720, 5,591,600 and 5,591,623, commonly assigned with this application, the disclosures of which are herein incorporated by reference).

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative, not limiting.

EXAMPLES

Example 1
N3-Benzyloxymethyl-2'-O-methoxycarbonylmethylene-5-methyluridine (2)

Sodium hydride (1.025 g, 25.6 mmol, 60% oil dispersion) was added to a solution of N3-benzyloxymethyl-5-methyluridine (9.70 g, 25.6 mmol) (prepared according to the procedure illustrated in U.S. patent application Ser. No. 08/464,953, filed Jun. 6, 1995) in anhydrous DMF (250 mL) at 5° C. The reaction mixture was allowed to warm to ambient temperature and stirred for 1 hour. The suspension was cooled to −40° C. in an $CH_3CN—CO_2$ bath and methyl 2-bromoacetate (2.36 mL, 25.6 mmol) was added slowly. The reaction mixture was allowed to slowly warm to ambient temperature over 1 hour, then stirred for 16 hours at ambient temperature. MeOH (10 mL) was added followed by addition of glacial AcOH (5 mL), and the reaction mixture was stirred for 5 minutes. The solvent was evaporated in vacuo to give an oil which was dissolved in EtOAc (500 mL), and the organic layer was washed with water (3×50 mL) and brine (50 mL). After drying the organic layer with $Na_2SO_4$, the solvent was evaporated in vacuo to give an oil which was dissolved in 2M $NEt_3$ in anhydrous MeOH (64 mL). After stirring at ambient temperature for 1 hour the solvent was evaporated in vacuo. The resulting oil was purified by column chromatography using $CH_2Cl_2$:MeOH (95/5, v/v) as the eluent to give 2.99 g (26%) of the title compound as a hygroscopic white foam. A second fraction with minor impurities gave 5.57 (~5%) of the title compound as a foam.

$^1$H NMR ($CDCl_3$): δ 7.63 (s, 1H), 7.30 (m, 5H), 5.72 (d, 1H, $J_{1',2'}$=3.0 Hz), 5.47 (s, 2H), 4.69 (s, 2H), 4.39 ($q_{a,b}$, 2H, $J_{a,b}$=17.6 Hz), 4.2–4.0 (m, 3H), 3.8–3.6 (m, 2H), 3.74 (s, 3H), 1.89 (s, 3H). $^{13}$C NMR ($CDCl_3$): δ 171.7, 163.3, 150.8, 137.6, 135.9, 128.1, 127.5, 127.4, 109.7, 90.3, 84.5, 83.5, 72.1, 70.3, 68.2, 67.9, 60.9, 52.2, 12.9. HRMS (FAB) calcd for $C_{21}H_{26}N_2O_9+Na^+$: 473.1536; found: 473.1549. 2D-$^1$H NMR (TOCSY) confirmed 2'-O-alkylation.

Example 2
2'-O-Methoxycarbonylmethylene-5-methyluridine (3)

Compound 2 (2.99 g, 6.64 mmol) was dissolved in anhydrous MeOH (80 mL) and added, under an argon atmosphere, to a pressure bottle containing 10% Pd on carbon (750 mg). The vessel was pressurized to 30 psi with hydrogen and shaken for 16 hours. The contents of the vessel were filtered through a celite pad and the filtrate evaporated in vacuo. The resulting oil was dissolved in 1M $NEt_3$ in anhydrous MeOH, and the solution was heated at reflux temperature for 2 hours. The solvent was evaporated in vacuo to give 2.735 g (95%) of the title compound as a white solid.

$^1$H NMR (DMSO-$d_6$): δ 11.4 (br s, 1H), 7.75 (s, 1H), 5.92 (d, 1H, $J_{1',2'}$=5.2 Hz), 5.19 (m, 2H), 4.24 (m, 2H), 3.87 (m, 1H), 3.63 (s, 3H), 1.78 (s, 3H). $^{13}$C NMR (pyridine-$d_5$) 171.3, 165.0, 152.1, 136.7, 110.2, 88.1, 85.S), 84.1, 69.6, 68.0, 61.0, 51.7, 12.7. LRMS (ES): m/z 352.E (M+Na)$^+$.

Example 3
5'-O-DMT-2'-O-methoxycarbonylmethylene-5-methyluridine (4)

4,4'-Dimethoxytrityl chloride (2.79 g, 8.24 mmol) was added to a solution of Compound 3 (39 mg, 0.32 mmol, dried by evaporation with anhydrous pyridine twice, then dried in vacuo (0.1 torr) for 12 hours at ambient temperature) and dimethylaminopyridine (39 mg, 0.32 mmol) dissolved in anhydrous pyridine (60 mL) with stirring for 12 hours. MeOH (10 mL) was added with stirring for 30 minutes and the solvent was evaporated in vacuo. The resulting oil was dissolved in EtOAc (500 mL) and the organic layer was washed with water (3×50 mL) then with brine (50 mL). $NEt_3$ (5 mL) was added, the organic layer was dried over $Na_2SO_4$, and the solvent was evaporated in vacuo. The resulting foam was purified by column chromatography using CH$_2$Cl$_2$:EtOAc (60/40, v/v) as the eluent to give 2.445 g (59%) of the title compound as a foam.

$^1$H NMR (CDCl$_3$): δ 7.69 (s, 1H), 7.43–6.81 (m, 13H), 5.93 (d, 1H, J$_{1',2'}$=2.6 Hz), 4.46 (q$_{a,b}$ 2H, J=17.2 Hz), 4.14 (m, 2H), 3.79 (s, 9H), 3.51 (m, 2H), 1.35 (s, 3H) $^{13}$C NMR (CDCl$_3$) 171.6, 164.2, 158.6, 150.5, 144.3, 135.3, 135.2, 130.0, 128.0, 127.9, 127.0, 113.2, 110.8, 87.9, 86.7, 84.5, 83.3, 68.4, 67.8, 61.7, 55.1, 52.2, 11.7. HRMS (FAB) calcd for C$_{34}$H$_{36}$N$_2$O$_{10}$+Cs$^+$: 765.1424. Found: 765.1452. Anal. Calcd for: C$_{34}$H$_{36}$N$_2$O$_{10}$:% C, 64.55;% H; 5.74;% N, 4.43. Found:% C, 65.01;% H; 5.79;% N, 4.54.

Example 4

5'-O-DMT-2'-O-methoxycarbonylmethylene-5-methyluridine-3'-(2-cyanoethyl-N,N-diisopropylphosphoramidite) (5)

Compound 4 (1.29 g, 2.04 mmol) was dissolved in CH$_2$Cl$_2$ (20 mL), diisopropylethylamine (0.78 mL, 4.48 mmol) and 2-cyanoethyl diisopropylchlorophosphoramidite (0.501 mL, 2.24 mmol) were added dropwise at ambient temperature. After stirring 1.5 hours at ambient temperature additional diisopropylethylamine (0.78 mL, 4.48 mmol) and 2-cyanoethyl diisopropylchlorophosphoramidite (0.501 mL, 2.24 mmol) were added dropwise at ambient temperature. After an additional hour EtOAc (200 mL) was added to the reaction mixture, the organic was washed with half-saturated NaHCO$_3$ twice, washed with brine, the organic was dried over MgSO$_4$ and evaporated in vacuo. The resulting oil was dissolved in CH$_2$Cl$_2$ and purified by silica gel column chromatography using CH$_2$Cl$_2$:EtOAc:NEt$_3$ (70/30/0.5, v/v/v) as the eluent to give 1.43 g of the title compound as an oil. Further elution using EtOAc:NEt, (95.5/0.5, v/v) as the eluent gave a second fraction of product. The product fraction was transferred to a round bottom flask and dissolved in CH$_2$Cl$_2$ (14 mL). Hexanes (200 mL) were added to the resulting solution with vigorous stirring to give a white gum and a slightly turbid supernatent. The mixture was allowed to settle for several hours, the supernatent was decanted off, and the gum was ashed with hexanes thrice. The hexane washes were decanted off and the product was dried in vacuo (0.1 torr) for 12 hour to give 917 mg of the title compound as a white foam. The second fraction of product was isolated as a white solid (118 mg, 7%).

$^{31}$P NMR (CDCl$_3$): 151.1, 151.0. HRMS (FAB) calcd for C$_{43}$H$_{53}$N$_4$O$_{11}$P+Cs$^+$: 965.2503. Found: 965.2489.

Example 5

2'-O-(Methoxycarbonylmethylene)adenosine (18a)

Adenosine (25.0 g, 93.5 mmol) was dissolved in DMF (900 mL) under an argon atmosphere. The resulting solution was cooled to –50° C., NaH (60% dispersion in mineral oil) (4.86 g, 122 mmol) was added in two portions, and the reaction mixture was allowed to warm to –30° C. and stirred for 30 minutes. After recooling the reaction mixture to –50° C., methyl 2-bromoacetate (11.5 mL, 122 mmol) was added dropwise, and the reaction was allowed to warm to ambient temperature. After stirring at ambient temperature for 1 hour, MeOH (100 mL) was added, the reaction was stirred for 10 minutes, and the solvent was evaporated in vacuo to give a foam. The product was coevaporated with EtOAc to afford the title compound as a crude solid which was of sufficient purity for use without further purification in subsequent reactions. A small portion of the product was purified by column chromatography and characterized.

$^1$H NMR (DMSO-d$_6$): δ 3.48 (s, 3H), 3.56–3.59 (m, 2H), 4.0 (m, 1H), 4.21 (q$_{a,b}$, 2H, J$_{a,b}$=17 Hz), 4.38 (dd, 1H), 5.63 (dd, 1H), 5.29 (d, 1H), 5.40 (dd, 2H), 6.02 (d, 1H), 7.37 (bd, 2H), 8.12 (s, 1H), 8.28 (s, 1H). HRMS (FAB) calcd for C$_{13}$H$_{17}$N$_5$O$_6$+H$^+$: 340.1257; found: 340.1257. 2D-$^1$H NMR (TOCSY) confirmed 2'-O-alkylation.

Example 6

5'-O-t-Butyldiphenylsilyl-2'-O-(methoxycarbonylmethylene)-adenosine (18)

2'-O-(Methoxycarbonylmethylene)adenosine (23 g, 67.8 mmol) as a crude material was dissolved in dry pyridine (500 mL), t-butyldiphenylsilyl chloride (21.2 mL, 81.3 mmol) was added, and the reaction mixture was stirred for 15 hours at ambient temperature. The solvent was evaporated in vacuo to a volume of 250 mL, EtOAc (1 L) was added and the solution was washed with water (200 mL), then brine (100 mL), and dried with MgSO$_4$. The solvent was evaporated in vacuo to give a residue which was dissolved in a minimum amount of EtOAc (40 mL), and this solution was added dropwise to a vigorously stirred solution of hexanes (4 L) to give a precipitate. The mixture was allowed to settle for 12 hours after which time the supernatent was decanted off, and the solid was filtered and washed with hexanes twice to give the title compound as a solid (46.68 g). A small portion of the product was purified by column chromatography and characterized.

$^1$H NMR (DMSO-d$_6$): δ 1.01 (s, 9H), 3.55 (s, 3H), 3.72–3.98 (m, 2H), 4.05 (m, 1H), 4.19–4.39 (dd, 2H), 4.53 (dd, 1H), 4.70 (t, 1H), 5.40 (d, 1H), 6.09 (d, 1H), 7.24–7.63 (m, 12H), 8.04 (s, 1H), 8.23 (s, 1H).

Example 7

5'-O-[(2,2-dimethyl-1,1-diphenyl-1-silapropoxy)methyl]-2'-O-((N,N-dimethylaminoethyleneamino)carbonylmethylene)adenosine (19a)

N,N-Dimethylethylenediamine (7.81 mL, 71 mmol) was added to Compound 18 (2.44 g, 4.22 mmol) dissolved in anhydrous DMF (21 mL) with stirring at ambient temperature for 20 hours. The reaction mixture was evaporated and the resulting oil was dissolved in EtOAc (420 mL), the organic was washed with water thrice (3×50 mL), brine, the organic was dried over MgSO$_4$, and the solvent was evaporated in vacuo to give 2.40 g (90%) of the title compound as a white solid.

$^1$H NMR (CDCl$_3$): δ 8.29 (s, 1H), 8.12 (s, 1H), 7.68–7.39 (m, 10H), 6.14 (d, 1H, J 1',2'=3.4 Hz), 5.56 (bs, 2H), 4.46 (m, 2H), 4.32 (s, 1H), 4.14 (m, 4H), 3.88 (m, 2H), 3.20 (m, 1H), 2.92 (d 1H, J=14.8 Hz), 2.54 (m, 2H), 2.28 (s, 6H), 1.07 (s, 9H).

Example 8

2'-O-(4,4'-dimethoxytrityl)-2'-O-(2-N-(2-methylthioethyl)-acetamido)-5-methyluridine (62)

Compound 4 (841 mg, 1.33 mmol) was dissolved in anhydrous THF (4.0 mL), 2-methylthioethylamine (0.622 mL, 6.65 mmol) was added, and after stirring for 20 hours at ambient temperature the solvent was evaporated in vacuo at 28° C. to give an oil which was dissolved in EtOAc (85 mL). The organic phase was washed with water (3×10 mL), brine (10 mL), and dried with MgSO$_4$. The solvent was evaporated in vacuo at 35° C. to give a foam which was purified by flash chromatography to give 790 mg (86%) of the title compound as a white foam.

$^1$H NMR (CDCl$_3$): δ 9.14 (bs, 1H), 7.69 (s, 1H), 7.41–6.83 (m, 13H), 5.92 (d, 1H, J$_{1',2'}$=2.4 Hz), 4.45 (m, 1H), 4.38 (q$_{a,b}$, 2H, J$_{a,b}$=15.2 Hz), 4.18 (m, 1H), 4.02 (m, 1H), 3.79 (s, 6H), 3.74 (m, 1H), 3.53 (m, 4H), 2.65 (t, 2H), 2.10 (s, 3H), 1.40 (s, 3H). $^{13}$C NMR (CDCl$_3$): δ 170.0, 164.1, 158.6, 151.1, 144.3, 135.3, 135.2, 135.0, 130.0, 128.0, 127.9, 127.0, 113.2, 111.2, 88.5, 86.7, 84.1, 83.3, 69.7, 68.3, 61.5, 55.1, 37.9, 33.3, 15.0, 11.8. LRMS (ES): 690.1 (M-H)

Example 9
5'-O-DMT-2'-O-methoxycarbonylmethylene-5-methyluridine-3'-O-succinate (4a)

Compound 4 (0.25 g, 0.38 mmol) was mixed with succinic anhydride (0.057 g, 0.57 mmol) and dimethylamino pyridine (0.023 g, 0.19 mmol). The mixture was dried over $P_2O_5$ in vacuo overnight at 40° C. The dried material was dissolved in dichloromethane (1 mL) and triethyamine (0.106 mL, 0.76 mmol) was added with stirring at ambient temperature under argon atmosphere for 4 hours. The reaction was diluted with dichloromethane (30 mL) and washed with 10% citric acid (ice cold, 30 mL) and water (30 mL). The organic phase was dried over anhydrous sodium sulphate and evaporated in vacuo. The resulting foam was purified by silica gel column chromatography using methanol: dichloromethane:pyridine (1/8.9/0.1, v/v/v) as the eluent to give 0.2 g (71%) of the title compound as a white foam.

$^1$H NMR (DMSO-$d_6$): Δ 11.46 (s, 1H), 7.48 (s, 1H) 7.41–7.21 (m, 9H), 6.89 (d, 4H, J=8.86 Hz), 5.93 (d, 1H, J=6.62 Hz), 5.33 (m, 1H), 4.50 (t, 1H, 5.86 Hz), 4.22 (s, 2H), 4.16 (brs, 1H), 3.73 (s, 6H), 3.56 (s, 3H), 3.40–3.19 (m, 4H), 1.4 (s, 3H). $^{13}$C NMR (CDCl$_3$): δ 172.25, 170.18, 163.99, 158.54, 150.96, 148.85, 143.93, 136.38, 135.46, 134.90, 129.89, 127.85, 126.98, 113.12, 111.11, 87.03, 86.06, 81.26, 79.91, 70.52, 67.04, 62.8, 54.99, 51.62, 29.58, 11.51. HRMS (FAB) Calcd for $C_{38}H_{40}N_2O_{13}Na^+$ 755.2428, Found= 755.2448.

Example 10
5'-O-DMT-2'-O-methoxycarbonylmethylene-5-methyluridine-3'-O-succinyl-CPG (4b)

Dimethyl formamide (DMF, 0.64 mL), 2-(1H-benzotriazole-1-yl)-1,2,3-tetramethyluronium tetrafluoroborate (TBTU, 0.83 g, 0.26 mmol) and 4-methyl morpholine (0.53 g, 0.52 mmol) were added to Compound 4a (0.19 g, 0.25 mmol) dried over $P_2O_5$ in vacuo. The mixture was vortexed until it became a clear solution. Anhydrous DMF (2.2 mL) and activated CPG (1.13 g, 115.2 μmol/g) were added and allowed to shake on a shaker for 18 hours. The mixture was filtered and the functionalized CPG washed thoroughly with DMF, dichloromethane and diethyl ether. The CPG was dried over $P_2O_5$ in vacuo. To cap the unfunctionalized sites on the CPG it was mixed with the capping reagents (Cap A=2 mL, Cap B=2 mL, Perseptive Biosystems Inc.) and allowed to shake on a shaker for 2 hours. It was then filtered and washed with acetonitrile and diethyl ether to give the functionalized CPG (200 mg). After drying in vacuo loading capacity was determined (1.20 g, 45.34 mmol/g).

Example 11
General procedure for the synthesis of modified oligonucleotides having at least one 2'-O-methoxycarbonylmethylene functionality (22)

Phosphoramidite 5 is dissolved in anhydrous acetonitrile to give a 0.1 M solution and loaded on to an Expedite Nucleic Acid System (Millipore) to synthesize oligonucleotides. Protocols supplied by Millipore are used for the synthesis. For the coupling of the amidite 5 coupling time was extended to 10 minutes and this step was carried out twice. Coupling efficiencies were greater than 95%. A solution of (1R)-(–)-(10-camphorsulfonyl)oxaziridine (CSO) (0.5 M) in acetonitrile was used as the oxidizing agent. 2'-Deoxy phosphoramidites and all other reagents used for the synthesis were from Perseptive Biosystems Inc. Various amines were used to functionalize the oligonucleotides as described in the following sections.

Example 12
General procedure for the synthesis of modified oligonucleotides having at least one 2'-O-N-[2-(dimethylamino)ethylacetamido] modification (23)

CPG bound oligonucleotides having 2'-O-methoxycarbonylmethylene functionality 22 are suspended in 50% N,N-dimethylethylenediamine in methanol and kept at ambient temperature 24 hours. Under these conditions amine conjugation occurred by a nucleophilic displacement of the methoxy group. At the same time oligonucleotides were deprotected from CPG and protecting groups on exocyclic amino and phosphate groups were also removed. Resulting mixtures were evaporated to dryness to give the 5'-O-DMT containing oligonucleotides which were purified by HPLC (Waters, C-4, 7.8×300 mm, A=50 mM triethylammonium acetate, pH=7, B=acetonitrile 5 to 60% B in 55 Min., flow 2.5 mL/min., λ260 nm). Detritylation with aqueous 80% acetic acid and evaporation followed by desalting by HPLC on Waters C-4 column gave the modified oligonucleotides (SEQ ID NOs. 1–4). Oligonucleotides were analyzed by HPLC, CGE and mass spectrometry.

TABLE I

| ISIS No. | SEQ ID NO: | Sequence | Mass Calculated/ Found | HPLC[a] (Ret.) Min |
|---|---|---|---|---|
| 32328 | 1 | 5'GCGT*T*T*T*T*T*T*-T*T*GC G3' | 6317.64/ 6318.12 | 19.39 |
| 32329 | 2 | 5'CTC GTA CT*T*T*T*C CGG TCC 3' | 5970.97/ 5969.30 | 19.51 |
| 32330 | 3 | 5'T*CC AGG T*GT* CCG CAT* C 3' | 5411.50/ 5410.00 | 18.72 |
| 32335 | 4 | 5'TTT TTT TTT TTT TTT T*T*T* T* 3' | 6295.21/ 6294.82 | 20.51 |

[a]Waters, C-18, 3.9 × 300 mm, A = 50 mM triethylammonium acetate pH = 7, B = acetonitrile 5 to 60% b in 55 min., flow 1.5 mL/min, λ = 260 nm. T* = 2'-O-N-[2-(dimethylamino)ethylacetamido] $^{5Me}$U.

ammonium acetate pH=7, B=acetonitrile 5 to 60% b in 55 min., flow 1.5 mL/min, λ=260 nm. T*=2'-O-N-[2-(dimethylamino)ethylacetamido] $^{5Me}$U.

TABLE II (Tm advantage of 2'-O-N-[2-(dimethylamino)ethylacetamido] modification)

| SEQ ID NO: | Sequence | Tm °C. | ΔTm/ mod Vs DNA | DTm/ mod Vs P = S |
|---|---|---|---|---|
| 1 | 5'GCG T*T*T* T*T*T* T*T*T* T*GC G 3' | 50 | 0.17 | 0.97 |
| 2 | 5'CTC GTA CT*T* T*T*C CGG TCC 3' | 61.52 | 0.07 | 0.87 |
| 3 | 5'T*CC AGG T*GT* CCG CAT* C 3' | 67.78 | 1.37 | 2.17 |

ΔTm/mod is against RNA versus unmodified DNA/° C. in the first column and versus unmodified deoxy phosphorothioate DNA/° C. in the second column.

Example 13
General procedure for the synthesis of modified oligonucleotides having at least one 2'-O-[(N-methyl)-acetamido] modification (24)

CPG bound oligonucleotides having 2'-O-methoxycarbonylmethylene functionalities (22) were treated with 40% N-methylamine in water at ambient temperature for 24 hours which also effects cleavage of bound oligonucleotides from the solid support (Table III). Protecting groups on exocyclic amino and phosphate groups were removed simultaneously. Mixtures were evaporated to dryness to give the 5'-O-DMT containing oligonucleotides. Oligonucleotides were purified using HPLC (Waters, C-4 , 7.8×300 mm, A=50 mM triethylammonium acetate, pH=7, B=acetonitrile 5 to 60% B in 55 Min. Flow 2.5 mL/min., λ260 nm), detritylated with aqueous 80% acetic acid and desalting by HPLC on Waters C-4 column to give the final modified oligonucleotides.

TABLE III (Oligonucleotides containing 2'-O-[(N-methyl)acetamido] modification

| SEQ ID NO./ ISIS # | Sequence | Mass Calcd./found | | HPLC[a] (Ret.) |
|---|---|---|---|---|
| 1/32384 | 5'GCG T*T*T* T*T*T* T*T*T* T*GC G 3' | 5746.64 | 5745.68 | 18.23 |
| 2/32381 | 5'CTC GTA CT*T* T*T*C CGG TCC 3' | 5741.57 | 5739.58 | 18.12 |
| 3/32382 | 5'T*CC AGG T*GT* CCG CAT* C 3' | 5182.10 | 5180.01 | 18.02 |
| 4/32383 | 5'TTT TTT TTT TTT TTT T*T*T* T* 3' | 6066.77 | 6065.76 | 19.98 |

[a]Waters, C-4, 3.9 × 300 mm, A = 50 mM triethylammonium acetate pH = 7, B = acetonitrile 5 to 60% b in 55 min., flow 1.5 mL/min, λ = 260 nm. T* = 2'-O-[(N-methyl)-acetamido]$^{5Me}$U.

Example 14

General procedure for the synthesis of modified oligonucleotides having at least one 2'-O-acetamido modification (25)

CPG bound oligonucleotides having 2'-O-methoxycarbonylmethylene functionalities were treated with saturated methanolic ammonia and heated at 55° C. for 12 hours to give the 2'-O-acetamido containing oligonucleotides (Table IV). Under these conditions oligonucleotides were deprotected from CPG and protecting groups on exocyclic amino and phosphate groups were also removed. Mixtures were evaporated to dryness to give the 5'-O-DMT containing oligonucleotides. Crude oligonucleotides were purified by HPLC (Waters, C-4 , 7.8×300 mm, A=50 mM triethylammonium actate, pH=7, B=acetonitrile 5 to 60% B in 55 Min., flow 2.5 mL/min., λ260 nm), detritylated with aqueous 80% acetic acid and desalted by HPLC using a Waters C-4 column to give the modified oligonucleotides.

TABLE IV (Oligonucleotide containing 2'-O-[acetamido] modification)

| SEQ ID NO:/ ISIS No. | Sequence | Mass Calcd./found | | HPLC[a] (Ret.) |
|---|---|---|---|---|
| 1/32387 | 5'GCG T*T*T* T*T*T* T*T*T* T*GC G 3' | 5606.44 | 5607.10 | 17.03 |
| 2/32385 | 5'CTC GTA CT*T* T*T*C CGG TCC 3' | 5685.49 | 5684.66 | 17.70 |
| 3/18126 | 5'T*CC AGG T*GT* CCG CAT* C 3' | 5126.02 | 5124.97 | 17.78 |
| 4/32386 | 5'TTT TTT TTT TTT TTT T*T*T* T* 3' | 6010.73 | 6010.45 | 19.25 |

[a]Waters, C-4, 3.9 × 300 mm, A = 50 mM triethylammonium acetate pH = 7, B = acetonitrile 5 to 60% b in 55 min., flow 1.5 mL/min, λ = 260 nm. T* = 2'-O-[(acetamido]$^{5Me}$U.

Example 15

General procedure for the synthesis of modified oligonucleotides having at least one 2'-O-[(N,N-diethyl)-acetamido] modification (26)

CPG bound oligonucleotides having 2'-O-methoxycarbonylmethylene functionalities are treated with diethyamine (2 mL) at ambient temperature for 24 hours to give 2'-O-(N,N-diethyl)acetamido oligonucleotides. Under these conditions oligonucleotides are deprotected from CPG and the protecting groups on exocyclic amino and phosphate groups are removed. Mixtures were further evaporated to dryness to give the 5'-O-DMT containing oligonucleotides. The oligonucleotides are further purified by HPLC (Waters, C-4, 7.8×300 mm, A=50 mM triethylammonium acetate, pH=7, B=acetonitrile 5 to 60% B in 55 Min., flow 2.5 mL/min., λ260 nm), detritylated using aqueous 80% acetic acid and desalted by HPLC using a Waters C-4 column to give the modified oligonucleotides.

Example 16

General procedure for the synthesis of modified oligonucleotides having at least one conjugated spermine group (27)

CPG bound oligonucleotides having at least one 2'-O-methoxycarbonylmethylene functionality (22) were suspended in a solution of spermine (1M) in methanol and kept at ambient temperature for 24 hours. The methoxy groups were displaced by the spermine via nucleophilic displacement, the modified oligonucleotide was cleaved from the CPG and the exocyclic amino and phosphate groups were also removed under these conditions. The solvent was removed by evaporation to give the 5'-O-DMT containing oligonucleotides. Excess spermine was removed by passing the modified oligonucleotides through a Sephadex G25 column. Oligonucleotides were further purified by HPLC (Waters, C-4 , 7.8×300 mm, A=50 mM triethyl ammonium actate, pH 7, B=acetonitrile 5 to 60% B in 55 Min., flow 2.5 mL/min., λ260 nm), detritylated with aqueous 80% acetic acid and desalted using HPLC with a Waters C-4 column to give the spermine modified oligonucleotides.

Example 17

General procedure for the synthesis of modified oligonucleotides having at least one conjugated spermidine group (28)

CPG bound oligonucleotides having at least one 2'-O-methoxycarbonylmethylene functionality (22) were suspended in a solution of spermidine (1M) in methanol and kept at ambient temperature for 24 hours. The methoxy groups were displaced by the spermidine via nucleophilic displacement, the modified oligonucleotide was cleaved from the CPG and the exocyclic amino and phosphate groups were also removed under these conditions. The solvent was removed by evaporation to give the 5'-O-DMT containing oligonucleotides. Excess spermidine was removed by passing the modified oligonucleotides through a Sephadex G25 column. Oligonucleotides were further purified by HPLC (Waters, C-4 , 7.8×300 mm, A=50 mM triethyl ammonium actate, pH=7, B=acetonitrile 5 to 60% B in 55 Min., flow 2.5 mL/min., λ260 nm), detritylated with aqueous 80% acetic acid and desalted using HPLC with a Waters C-4 column to give the spermidine modified oligonucleotides.

Example 18

General procedure for the synthesis of modified oligonucleotides having at least one conjugated peptide group (29)

CPG bound 5'-O-DMT-oligonucleotides having at least one 2'-O-methoxycarbonylmethylene functionality are suspended in a solution of oligopeptides (0.1M) (including e.g., Lys-Tyr-Lys; Lys-Trp-Lys; and Lys-Lys-Lys-Lys) in dimethyl formamide (DMF) and kept at ambient temperature for 24 hours. DMF was evaporated and the residues were mixed with aqueous ammonium hydroxide (2 mL) with heating at 55° C. for 6 hours. The mixtures were evaporated to dryness to give the 5'-O-DMT containing oligonucleotides. Modified oligonucleotides were purified by HPLC (Waters, C-4, 7.8×300 mm, A=50 mM triethyl ammonium acetate, pH=7, B=acetonitrile 5 to 60% B in 55 Min., flow 2.5 mL/min., λ260 nm), detritylated using aqueous 80% acetic acid and desalted by HPLC using a Waters C-4 column to give the peptide modified oligonucleotides.

Example 19
General procedure for the synthesis of modified oligonucleotides having at least one cholesterol group (30)

To a CPG bound oligonucleotide having a 2'-O-methoxycarbonylmethylene functionality (see Example 10 et al.) is added a solution of cholesterol hexylamine conjugate in a mixture of chloroform and ethanol. The mixture is kept at room temperature for several hours. The progress of the reaction is monitored by HPCL. When the reaction has gone to completion the product is deprotected following standard protocols to give the conjugated oligonucleotide 30.

Example 20
Folic acid conjugated 5-methyluridine (31) To a CPG bound oligonucleotide having a 2'-O-methoxycarbonylmethylene functionality (see Example 10 et al.) is added a solution of hexylamine conjugated folic acid in DMF. The reaction mixture is kept at room temperature and monitored by HPLC. Upon completion of the reaction the product is deprotected and purified following standard protocols to give the conjugated oligonucleotide 31.

Example 21
5-Methyl-tetrahydrofolic acid conjugated 5-methyluridine (32)

To a CPG bound oligonucleotide having a 2'-O-methoxycarbonylmethylene functionality (see Example 10 et al.) is added a solution of hexylamine conjugated 5-methyltetrahydro folic acid in DMF. The reaction mixture is kept at room temperature and monitored by HPLC. Upon completion of the reaction the product is deprotected and purified following standard protocols to give the conjugated oligonucleotide 32.

Example 22
2'-O-Methoxycarbonylmethyleneadenosine (41)

Sodium hydride (4.86 g, 1.3 eq., 122 mM, 60% dispersion in mineral oil) was washed with hexanes and added in two portions to a mixture of adenosine (25 g, 93.5 mM) dissolved in DMF (900 mL) at −50° C. with stirring until the outside temperature was −30° C. The mixture was again cooled to −50° C. and methyl-2-bromoacetate was added to the reaction dropwise. The reaction was stirred until it warmed to room temperature. After another hour the NaH was quenched with MeOH (100 mL). The mixture was then concentrated down to a foam by and coevaporation with ethyl acetate (EtOAc). No further purification was necessary for the next synthetic step.

$^1$H NMR (DMSO) δ 3.48 (s, 3H), 3.56–3.59 (m 2H), 4.0 (m, 1H), 4.21(q, 2H), 4.38 (dd, 1H), 5.63 (dd, 1H), 5.29 (d, 1H), 5.40 (dd, 2H), 6.02 (d, 1H), 7.37 (bd, 2H), 8.12 (s,1H), 8.28 (s, 1H). 2D TOCSY NMR confirmed 2' alkylated product by showing no 2D correlation of the 2' hydrogen to an OH and found a correlation between the 3' hydrogen and the 3'—OH. HRMS (FAB) m/z [MH]$^+$ 340.1257 ($C_{13}H_{17}N_5O_6$ requires 339.1178).

Example 23
5,-O-TBDPSi-2'-O-methoxycarbonylmethyleneadenosine (42)

2'-O-Methoxycarbonylmethyleneadenosine (41) (approximately 23 g) from Example 22 was dissolved in dry pyridine (500 mL) and t-butylchlorodiphenylsilane (TBDPSi-Cl) (21.15 mL, 1.2 eq., 81.34 mM) was added. The reaction was stirred overnight and reached completion as determined by tlc. The reaction solvent volume was then reduced by approximately half (~250 mL) in vacuo with the remainder partitioned between EtOAc and H$_2$O. The product was extracted into the EtOAc, which was washed once with brine (100 mL), dried with MgSO$_4$, filtered and evaporated in vacuo. The residue was then dissolved into a minimal amount of EtOAc (~40 mL) and slowly dropped into 4 liters of vigorously stirred dry Ethyl Ether (Et$_2$O). The product precipitated from the solution mixture. The mixture was allowed to settle overnight at which time the solvent was decanted off. The solid left behind was collected by filtration and washed with Et$_2$O. 46.68 g of crude product solid was collected.

$^1$H NMR (DMSO) δ 1.01 (s, 9H), 3.55 (s, 3H), 3.72–3.98 (m, 2H), 4.05 (m, 1H), 4.19–4.39 (dd, 2H), 4.53 (dd, 1H), 4.70 (t, 1H), 5.40 (d, 1H), 6.09 (d, 1H), 7.24–7.63 (m, 12H), 8.04 (s, 1H), 8.23 (s, 1H). HRMS: calculated for $C_{32}H_{43}N_7O_5Si$ 634.3173, found 634.3166.

Example 24
5'-O-TBDPSi-2'-O-((N,N-dimethylaminoethyleneamino) carbonylmethylene)adenosine (43)

Compound 42 (2.44 g, 4.22 mmol) was dissolved in anhydrous DMF (21 mL), N,N-dimethylethylenediamine (7.81 mL, 71 mmol) was added and the reaction mixture was stirred at ambient temperature for 20 hours. The mixture was concentrated to an oil which was dissolved in EtOAc (420 mL), the organic was washed with water (3×50 mL), brine (1×50 mL), and the organic was dried with MgSO$_1$, and the solvent was evaporated in vacuo to give 2.40 g (90%) of the title compound as a white solid.

$^1$H NMR (CDCl$_3$): δ 8.29 (s, 1H), 8.12 (s, 1H), 7.68–7.39 (m, 10H), 6.14 (d, 1H, J 1',2'=3.4 Hz), 5.56 (bs, 2H), 4.46 (m, 2H), 4.32 (s, 1H), 4.14 (m, 4H), 3.88 (m, 2H), 3.20 (m, 1H), 2.92 (d 1H, J=14.8 Hz), 2.54 (m, 2H), 2.28 (s, 6H), 1.07 (s, 9H).

Example 25
5'-O-TBDPSi-2'-O-((N,N-dimethylaminoethyleneamino) carbonylmethylene)-N6-benzoyladenosine (44)

Compound 43 (23.21 g, 14.71 mmol) was dissolved in dry Pyridine (160 mL) and cooled in an ice bath. Chlorotrimethylsilane (11.78 mL, 92.84 mmol) was added dropwise and the reaction was stirred for 30 minutes at which time benzoylchloride (10.87 mL, 92.84 mmol) was added dropwise to the reaction. The ice bath was removed after 30 minutes and the reaction was stirred for 3 hours. The reaction was once again cooled in an ice bath. Water (32 mL) was added followed with concentrated NH$_4$OH (32 mL) after 30 minutes. After 1 hour the reaction was partitioned between water and ethyl acetate (200/200 mL ). The aqueous layer was extracted twice more with ethyl acetate (50 mL). The ethyl acetate extracts were pooled and washed once with brine (50 mL), dried with MgSO$_4$, filtered and evaporated in vacuo to an oil. The resulting crude material was purified by silica gel column chromatography using Et$_2$N:MeOH:EtOAc:CHCl$_3$ (2/5/60/33, v/v/v/v) as the eluent. The appropriate fractions were collected and concentrated in vacuo to afford 15.13 g (88%) of title compound.

$^1$H NMR (CDCl$_3$): δ 1.07 (s, 9H), 2.28 (s,6H), 2.58 (m, 2H), 3.06 (m, 1H), 3.84 (m, 3H), 4.08–4.52 (m, 6H), 6.21

(d,1H), 7.27–7.69 (m, 12H), 8.00 (d,3H), 8.31 (s,1H), 8.73 (s,1H), 9.15 (bs, 1H).

Example 26

2'-O-((N,N-dimethylaminoethyleneamino) carbonylmethylene)-N6-benzoyladenosine (45)

Tetrabutylammoniumfloride (70 mL, 70.15 mmol, 1M) in THF was added to compound 44 (14.82 g, 23.38 mmol) dissolved in THF (200 mL) with stirring. After 4 hours the reaction had reached completion as indicated by tlc. The solvent was evaporated leaving a yellowish orange oil which was purified by silica gel column chromatography using Et$_2$N:MeOH:CHCl$_3$ (3/5/92, v/v/v) as the eluent. The appropriate fractions were pooled and concentrated to afford 7.06 g (60%) of the title compound.

$^1$H NMR (CDCl$_3$): δ 2.29 (s,6H), 2.52 (m 2H), 3.16 (m, 1H), 3.65–4.05 (m, 5H), 4.2.–4.42 (m, 4H), 4.71 (m,1H), 6.04 (s, 1H), 7.67 (m, 4H), 8.03 (d, 1H), 8.16 (s, 1H), 8.76 (s, 1H).

Example 27

5'-O-DMT-2'-O-((N,N-dimethylaminoethyleneamino) carbonylmethylene)-N6-benzoyladenosine (46)

Compound 45 (7.09 g, 15.77 mmol) was co-evaporated with pyridine three times before being dissolved in dry pyridine (250 mL). 4,4'-Dimethoxytritylchloride (6.95 g, 20.50 mmol) was added in two portions to the reaction mixture. TLC at 20 hours showed reaction to be complete. The solvent volume was reduced to half by evaporation in vacuo. The residue was partitioned between EtOAc (200 mL) and water (200 mL). The aqueous phase was extracted with EtOAc (2×50 mL). The EtOAc was pooled, dried over MgSO$_4$, filtered and concentrated in vacuo. The residue was purified by silica gel column chromatography using luting with MeOH:CHCl$_3$ (5/95, v/v) as the eluent. The appropriate fractions were collected and concentrated to afford 6.33 g (56%) of title compound.

$^1$H NMR (CDCl$_3$)δ 2.28 (s, 6H), 2.54 (m, 2H), 3.12 (m, 1H), 3.49 (m, 2H), 3.81 (s, 7H), 4.12 (s, 1H), 4.38 (m, 3H), 4.63 (t, 1H), 6.20 (d, 1H), 6.84 (d, 4H), 7.26–7.62 (m, 13H), 8.03 (d, 2H), 8.24 (s, 1H), 8.74 (s, 1H), 9.13 (bs, 1H). HRMS: calculated for C$_{44}$H$_{47}$N$_7$O$_8$+Na 824.3384, found 824.3379.

Example 28

5'-O-DMT-2'-O-((N,N-dimethylaminoethyleneamino) carbonyl-methylene)-N6-benzoyladenosine-3'-(2-cyanoethyl-N,N-diisopropylphosphoramidite) (47)

2-Cyanoethyl-N,N,N',N'-tetraisopropylphosphoramidite (2.41 mL, 7.59 mmol) was added dropwise to a mixture of Compound 46 dissolved in CH$_2$Cl$_2$ (100 mL) and diisopropylamine tetrazolide (1.19 g, 6.95 mmol) with stirring overnight. The reaction was diluted with EtOAc (200 mL) and extracted with saturated NaHCO$_3$ (100 mL) twice, then washed once with brine (100 mL). The EtOAc was then dried over MgSO$_4$, filtered and concentrated. The residue was dissolved in a minimal amount of CH$_2$Cl$_2$ (5 mL) and vigorously stirred while dry hexane (250 mL) was added to precipitate the title compound. The solvents were decanted away from the precipitate and the residue dried in vacuo and the precipitation was repeated once more to yield 5.91 g (93%) of the title compound.

$^{31}$P NMR (CDCl$_3$): δ 151.08 and 151.41.

Example 29

5'-TBDPSi-2'-O-((N,N-dimethylaminoethyleneamino) carbonylmethylene)-guanosine-3'-(2-cyanoethyl-N,N-diisopropylphosphoramidite) (48)

Guanosine was reacted with methyl-2-bromoacetate as per the procedure illustrated above in Example 22. The resulting 2'-O-(methoxycarbonylmethylene)guanosine (48a) was treated as per the procedure illustrated in Example 23 above to give 5'-O-TBDPSi-2'-O-(methoxycarbonylmethylene)guanosine (48b).

N,N-Dimethylethylenediamine (36.98 mL, 337 mmol) was added to 5'-O-TBDPSi-2'-O-(methoxycarbonylmethylene)guanosine (20 g, 33.69 mmol) dissolved in DMF (200 mL) via dropping funnel with stirring overnight. The solvent volume was reduced by half in vacuo and the resultant mixture was partitioned between EtOAc (500 mL) and water (500 mL). The water was further extracted twice with EtOAc (100 mL). The EtOAc was pooled and washed twice with water (100 mL) and once with brine (100 mL), dried over MgSO$_4$, filtered and concentrated. During the evaporation of the EtOAc a white precipitate formed and was filtered. The filtrate was then concentrated to a yellowish foam in vacuo. Proton NMR of the precipitate and the foam were consistent with the desired product structure. Combined product fractions gave 18.20 g (83%) of title compound.

$^1$H NMP (DMSO): δ 0.976 (s,9H), 2.10 (s, 6H), 2.26 (t, 2H), 3.21 (q, 2H), 3.84 (m, 2H), 4.02 (d, 3H), 4.37 (bs, 2H), 5.66 (bs, 1H), 5.92 (s, 1H), 6.50 (bs, 2H), 7.40 (m, 8H), 7.60 (d, 2H), 7.81 (s, 2H), 10.64 (bs, 1H). HRMS calculated for: for C$_{32}$H$_{43}$N$_7$O$_6$Si+Na 672.2942, found 672.2932.

Example 30

5'-O-[(2,2-dimethyl-1,1-diphenyl-1-silapropoxy)methyl]-2'-O-((N,N-dimethylaminoethyleneamino) carbonylmethylene)-N2-isobutrylguanosine (49)

Compound 48 (7.05 g, 10.85 mmol) was dissolved in 130 mL pyridine and cooled in an ice bath. Chlorotrimethylsilane (5.51 mL, 43.40 mmol) was added dropwise and the reaction mixture was stirred at 0° C. for 30 minutes at which time isobutyryl chloride (7.20 mL, 43.40 mmol) was added to the reaction mixture dropwise and stirred for 1 hour before the ice bath was removed. The reaction mixture was stirred for another 3 hours at which time the reaction was cooled in an ice bath and H$_2$O (26 mL) was added with stirring for 30 minutes. Concentrated NH$_4$OH (26 mL) was added with stirring for one hour at which time tlc indicated that the reaction had gone to completion. The reaction mixture was partitioned between EtOAc (250 mL) and H$_2$O (250 mL). The organic phase was extracted twice with water (100 mL), washed with brine (100 mL), dried over MgSO$_4$1 filtered and concentrated. Drying gave 6.71 g (86%) of the title compound. The material was used without further purification.

$^1$H NMR (CDCl$_3$): δ 1.03 (s, 9H), 1.25 (d, 6H), 2.20 (s, 6H),2.51 (bs, 2H), 2.71 (m, 1H), 3.10 (m, 1H), 3.80 (m, 3H), 4.09–4.52 (m, 6H), 5.88 (d, 1H), 77.44 (m 8H), 7.70 (m, 2H), 7.90 (s, 1H), 9.72 (bs, 1H).

Example 31

2'-O-((N,N-dimethylaminoethyleneamino) carbonylmethylene)-N2-isobutrylguanosine (50)

Tetrabutylammoniumfloride (32.88 mL, 32.88 mmol, 1M) in THE was added to Compound 49 (7.89, 10.96 mmol) dissolved in THF (100 mL) with stirring overnight. The tlc of the mixture showed completion of reaction. The solvent was removed in vacuo and the residue purified by silica gel column chromatography. Concentration of appropriate fractions gave 4.93 g (92%) of the title compound having minor impurities associated with ammonium salts.

$^1$H NMR (DMSO): δ tetrabutylammonium salts obscure the region form 0.86–1.59ppm. 2.17 (s, 6H), 2.27 (t, 2H), 2.6.–2.77 tetrabutylammonium salts. 3.38–3.66 (m, 3H), 3.95–4.01 (m, 3H), 4.44 (m, 1H), 4.57 (t, 1H), 5.93 (s,1H), 7.97 (bt, 1H), 8.26 (s, 1H).

Example 32
5'-O-DMT-2'-O-((N,N-dimethylaminoethyleneamino) carbonylmethylene)-N2-isobutrylguanosine (51)

4,4'-Dimethoxytritylchloride (4.83 g, 14.25 mmol) was added in one portion to a solution of Compound 50 (4.93 g, 1.02 mmol, crude) dissolved in dry pyridine (70 mL) with stirring overnight. The reaction went to completion as indicated by tlc. The solvent was reduced by two thirds the volume and partitioned between EtOAc (200 mL) and water (200 mL). The water was extracted twice with EtOAc (50 mL). The EtOAc was pooled and washed once with brine (100 mL), dried over $MgSO_4$, filtered and concentrated. The residue was passed through three silica gel columns ($1^{st}$ column: $3°$ $Et_2N/10\%$ $MeOH/CHCl_3 2^{nd}$ and $3^{rd}$ column: 10% $MeOH/CHCl_3$) to obtain 3.44 g (40%) of the title compound containing minor amounts of tetrabutylammonium salt and triethylamine impurities.

$^1H$ NMR ($CDCl_3$): δ 1.13 (d, 6H), 2.64 (s, 6H), 3.91 (m, 2H), 3.31 (m, 2H), 3.46 (m, 1H), 3.77 (s, 6H), 4.38 (m, 2H), 4.61 (m, 2H), 5.98 (d, 1H), 6.79 (d, 4H), 7.18–7.44 (m, 9H), 7.80 (s, 1H), 8.57(bs,1H).

Example 33
5'-O-DMT-2'-O-((N,N-dimethylaminoethyleneamino) carbonylmethylene)-N2-isobutrylguanosine-3'-(2-cyanoethyl-N,N-diisopropylphosphoramidite) (52)

To a solution of Compound 51 (2.88 g, 3.67 mmol) dissolved in dry $CH_2Cl_2$ and diisopropylamine tetrazolide (692 mg, 4.04 mmol) was added 2-cyanoethyl-N,N,N',N'-tetraisopropylphosphoramidite (1.40 mL, 4.41 mmol) with stirring overnight. The reaction went to completion as indicated by tlc. The reaction was diluted with EtOAc (100 mL) and extracted with saturated $NaHCO_3$ (50 mL) twice and washed once with of brine (50 mL). The mixture was dried over $MgSO_4$, filtered and concentrated. The residue was dissolved in dry $CH_2Cl$ (4 mL) and stirred vigorously with hexane (200 mL) added to precipitate the amidite. This precipitation was performed twice to obtain 3.15 g (87%, with tetrabutylammonium salt impurities).

$^{31}P$ NMR ($CDCl_3$): δ 148.70ppm and 149.91ppm.

Example 34
5'-O-DMT-2'-O-(2-N,N-dimethylacetamido)-5-methyluridine (53)

5'-O-DMT-2'-O-methoxycarbonylmethylene-5-methyluridine (Compound 4) (1.00 g, 1.58 mmol) was dissolved in 2.0 M dimethylamine in THF, the reaction flask was sealed with a septum, and the reaction mixture was stirred at ambient temperature for 18 hours. The solvent was evaporated in vacuo at ambient temperature to give 0.97 g (95%) of the title compound as a foam.

$^1H$ NMR ($CDCl_3$): δ 7.73 (s, 1H), 7.45–6.80 (m, 13H), 5.87 (d, 1H, $J_{1',2'}$=1.0 Hz), 4.57 ($q_{ab}$, 2H), 4.46 (m, 1H), 4.23 (m, 1H), 4.02 (m, 1H), 3.77 (s, 6H), 3.52 (m, 2H), 2.96 (s, 3H), 2.91 (s, 3H), 1.35 (s, 3H). $^{13}C$ NMR ($CDCl_3$): 170.0, 164.2, 158.5, 150.7, 144.4, 135.4, 135.3, 135.0, 130.0, 128.0, 127.8, 127.5, 126.8, 113.1, 110.5, 89.0, 86.5, 85.7, 83.4, 68.5, 61.5, 55.0, 35.5, 35.3, 11.7. HRMS (FAB) calcd for $C_{35}H_{39}N_3O_9+Na^+$: 668.2584. Found: 668.2561.

Example 35
5'-O-DMT-2'-O-(2-N,N-dimethylacetamido)-5-methyluridine-3'-(2-cyanoethyl-N,N-diisopropylphosphoramidite) (54)

Diisopropylamine tetrazolide (146 mg, 0.86 mmol) and 2-cyanoethyl-N,N,N',N'-tetraisopropylphosphorodiamidite (0.54 mL, 1.70 mmol) were added to a solution of Compound 53 (914 mg, 1.42 mmol) dissolved in $CH_2Cl_2$ (14 mL). Three additional portions of 2-cyanoethyl-N,N,N',N'-tetraisopropylphosphorodiamidite (3×0.54 mL, 1.70 mmol) was added over a period of 10 hours. EtOAc (120 mL) was added and the volume was reduced by about 15 mL of solvent via evaporation in vacuo. The organic phase was washed with saturated $NaHCO_3$ (3×12 30 mL), then with brine (2×12 mL), and dried over $MgSO_4$. The solvent was evaporated in vacuo at 27° C. to give an oil which was dissolved in $CH_2Cl_2$ (4 mL), then hexanes (200 mL) were slowly added to the rapidly stirred solution via addition funnel to give a wax. The supernatant was decanted, the wax was washed with hexanes thrice and the washes were decanted. The precipitation was repeated two additional times to give a white wax which was dried in vacuo at ambient temperature to give 1.09 g (91%) of the title compound as a foam.

$^{31}P$ NMP ($CD_2Cl_2$): δ 152.9, 152.8. HRMS (FAB) calcd for $C_{44}H_{56}N_5O_{10}P+Na^+$: 868.3663. Found: 868.3691.

Example 36
5'-O-DMT-2'-O-(2-N-[2-(dimethylamino)ethyl]-acetamido)-5-methyluridine (55)

N,N-dimethylethylenediamine (18.7 mL, 170 mmol) was added to a solution of Compound 1 (5.378 g, 8.50 mmol) dissolved in anhydrous THF (66 mL) with stirring at ambient temperature for 6 hours. Toluene (80 mL) was added and the solvent was evaporated in vacuo to give 6.12 g (95%) of the title compound as a white foam.

$^1H$ NMR ($CDCl_3$): δ 7.64 (s, 3H), 7.41–6.79 (m, 13H), 5.94 (d, 1H, $J_{1',2'}$=2.4 Hz), 4.41 (m, 1H), 4.31 ($q_{ab}$, 2H), 4.19 (m, 1H), 3.95 (m, 1H), 3.75 (s, 6H), 3.52 (m, 2H), 2.75 (m, 2H), 2.48 (m, 2H), 2.24 (s, 6H), 1.36 (s, 3H). $^{13}C$ NMR ($CDCl_3$): δ 170.1, 164.7, 158.7, 151.0, 144.4, 135.5, 135.3, 134.9, 130.1, 129.0, 128.1, 127.7, 127.1, 113.3, 110.9, 88.5, 86.7, 84.8, 83.3, 70.7, 68.2, 61.8, 58.4, 45.4, 36.0, 12.0. 25 HRMS (MALDI) calcd for $C_{37}H_{44}N_4O_9+Na^+$: 711.3006. Found: 711.3001. Tlc: $CH_2Cl_2$-EtOAc-MeOH-$NEt_3$, 64:21:21:5, v/v/v/v; $R_f$ 0.4.

Example 37
5'-O-DMT-2'-O-(2-N-[2-(dimethylamino)ethyl]-acetamido)-5-methyluridine-3'-(2-cyanoethyl-N,N-diisopropylphosphoramidite) (56)

Diisopropylamine tetrazolide (715 mg, 4.183 mmol) and 2-cyanoethyl-N,N,N',N'-tetraisopropylphosphorodiamidite (3.18 mL, 10.02 mmol) were added to a solution of Compound 55 (5.754 g, 8.35 mmol) which was dried by coevaporation with anhydrous pyridine (2×75 mL) dissolved in $CH_2Cl_2$ (60 mL). The reaction mixture was stirred for 13 hours and EtOAc (420 mL) was added. The volume of solvent was reduced by about 60 mL by evaporation in vacuo. The organic phase was washed with half-saturated $NaHCO_3$ (3×80 mL), then with brine (2 x 40 mL), and dried over $MgSO_4$. The solvent was evaporated in vacuo at 27° C. to give an oil which was coevaporated with toluene (2×300 mL). The resulting foam was dissolved in $CH_2Cl_2$ (20 mL) and hexanes (1000 mL) were slowly added to the rapidly stirred solution via addition funnel to give a wax. The supernatant was decanted, the wax was washed with hexanes thrice and the washes were decanted. The precipitation was repeated an additional time to give a white wax which was dried in vacuo at ambient temperature to give 6.60 g (89%) of the title compound as a foam.

$^{31}P$ NMR ($CDCl_3$): δ 151.5, 151.0.

Example 38
2'-O-(2-N-[2-(dimethylamino)ethyl]-acetamido)-5-methyluridine (57)

N,N-dimethylethylenediamine (50 mL, 456 mmol) was added to Compound 3 (11.46 g, 34.7 mmol) dissolved in anhydrous DMF (178 mL) with stirring at ambient temperature for 16 hours. The solvent was evaporated in vacuo to give an oil to which p-xylene (200 mL) was added. The solvent was evaporated in vacuo to give 15.64 g of the title compound as a foam. A small amount of this crude product (230 mg) was triturated with $Et_2O$ (3×5 mL) to give a white solid which was used for analytical data.

$^1$H NMR (DMSO-$d_6$): δ 11.35 (bs, 1H), 7.79 (s, 1H), 5.82 (d, 1H, $J_{1',2'}$=4.0 Hz), 4.00 (m, 4H), 3.90 (m, 1H), 3.16 (m, 2H), 2.27 (m, 2H), 2.12 (s, 6H), 1.74 (s, 3H). $^{13}$C NMR (pyridine-$d_5$): δ 170.0, 164.7, 151.7, 136.0, 109.8, 88.6, 85.2, 85.1, 70.7, 68.6, 60.2, 58.4, 45.0, 36.9, 12.5. HRMS (MALDI) calcd for $C_{16}H_{26}N_4O_7$+$Na^+$: 409.1699. Found: 409.1711. Tlc: $CH_2Cl_2$-EtOAc-MeOH-$NEt_3$, 57:19:19:5, v/v/v/v; $R_f$ 0.3

Example 39
2'-O-2-acetamido-5-methylcytidine (58)

Compound 57 (13.4 g, 34.7 mmol) was converted as per established literature procedures to the cytidine derivative (Divakar, K., Reese, C. B., *J. Chem. Soc. Perk., Trans I*, 1982, 1171). The final treatment of the product with methanolic ammonia resulted in a white precipitate which was filtered and washed with MeOH to give 2.186 g of the title compound as a white solid.

$^1$H NMR (DMSO-$d_6$): δ 7.77 (s, 1H), 7.48 (bs, 1H), 7.38 (bs, 1H), 7.35 (bs, 1H), 6.80 (bs, 1H), 5.76 (d, 1H, $J_{1',2'}$=3.0 Hz), 5.15 (bs, 1H), 4.06 (m, 3H), 3.77 (m, 4H), 1.80 (s, 3H). LRMS (ES), m/z: 337.2 (M+Na)$^+$.

Example 40
2'-O-(2-N-[2-(dimethylamino)ethyl]-acetamido)-5-methylcytidine (59)

Compound 58 (314 mg, 1.0 mmol) was dissolved in hot DMF (4.4 mL) followed by the addition of N,N-dimethylethylenediamine (4.4 mL, 40 mmol) with stirring and heating at 100° C. for 16 hours. The solvent was evaporated in vacuo to give a small volume of liquid (3 mL) to which $Et_2O$ (25 mL) was slowly added to give an oil. The supernatent was decanted, the oil was dissolved in MeOH (1 mL), and $Et_2O$ (50 mL) was slowly added with stirring to give an oil. The supernatent was decanted and the product was evaporated in vacuo to give 328 mg (85%) of the title compound as a foam.

$^1$H NMR (DMSO-$d_6$): δ 7.77 (s, 1H), 5.77 (d, 1H, $J_{1',2'}$=2.6 Hz), 5.45 (d, 1H), 5.17 (t, 1H), 4.05 ($q_{ab}$, m, 3H), 3.76 (m, 4H), 3.17 (dd, 2H), 2.28 (t, 2H), 2.12 (s, 6H), 1.80 (s, 3H). HRMS (MALDI) calcd for $C_{16}H_{27}N_5O_6$+$Na^+$: 408.1859. Found: 408.1867. Tlc: $CH_2Cl_2$-EtOAc-MeOH-$NEt_3$, 50:17:28:5, v/v/v/v; R, 0.25.

Example 41
5-O-DMT-2'-O-[(N,N-dimethyl)acetamido]-3'-O-succinyl-5-methyluridine (60)

Compound 53 (0.2 g, 0.3 mmol) was mixed with succinic anhydride (0.06 g, 0.61 mmol) and dimethylamino pyridine (0.04 g, 0.38 mmol). The mixture was dried over $P_2O_5$ in vacuo overnight. Dichloroethane (0.9 mL) was added and the reaction mixture was stirred at ambient temperature for 4 hours. $CH_2Cl_2$ (50 mL) was added and the organic layer was washed with ice cold aqueous citric acid (10% solution, 40 mL) and brine (40 mL). The organic phase was dried over anhydrous $Na_2SO_4$ and concentrated to dryness to give 0.22 g (96%) of the title compound as a foam.

Rf=0.42, 10% MeOH in $CH_2Cl_2$; $^1$H NMR (200 MHZ, $CDCl_3$) δ 1.38 (s, 3H), 2.67 (m, 4H), 2.95 (s, 3H), 2.97 (s, 3H), 3.34 (dd, 1H J=2.06 Hz, J=9.06 Hz), 3.59 (d, J -=9.28 Hz) 3.80 9s, 6h), 4.28–4.54 (m, 4H), 5.42 (t, 1H, J=5.38 Hz), 6.84 (d, 4H, J=8.3 Hz), 7.21–7.40 (m, 9H), 7.71 (s, 1H); $^{13}$C NMR (50 MHZ, $CDCl_3$) δ 11.57, 29.11, 29.26, 35.41, 36.05 55.13, 62.17, 68.39, 70.39, 79.83, 81.02, 87.02, 111.04, 127.06, 128.04, 130.01, 135.07, 135.87, 147.97, 150.81, 158.62, 164.81, 171.49, 175.3 MS (FAB) m/z 768 (M+Na)$^+$.

Example 42
5-O-DMT-2'-O-[ (N,N-dimethyl) acetamido] -3'-O-succinyl-5-methyluridine-3'-O-succinyl-CPG (61)

Anhydrous DMF (0.9 mL) was added to Compound 60 (0.22 g, 0.29 mmol) that was dried in vacuo overnight followed by 2-(1H-Benzotriazole-1yl)1,1,3,3-tetramethyluronium tetrafluoroborate (0.1 g, 0.3 mmol) and 4-methyl morpholine (65 μL, 0.59 mmol) with vortexing to give a clear solution. CPG (1.28 g, 118.9 μmol/g, particle size 80/120, mean pore diameter 569 Å) was added and allowed to shake on a shaker at ambient temperature for 18 hours. An aliquot was withdrawn and washed with DMF, $CH_3CN$ and $Et_2O$ and dried in vacuo. Loading capacity was determined by following standard procedure (58.46 μmol/g). Functionalized CPG was then washed with DMF, $CH_3CN$ and $Et_2O$ dried in vacuo. Unfunctionalized sites on the CPG were capped with acetic anhydride/collidine/N-methyl imidazole in THF (2 mL Cap A and 2 mL Cap B solutions from perspective Biosystems Inc.) and allowed to shake on a shaker for 2 hours. The CPG was filtered, washed with $CH_3CN$ and $Et_2O$ and dried in vacuo. The final loading capacity was determined to be 57.89 μmol/g.

TABLE V

Oligonucleotides containing 2'-O-[(N,N-dimethyl)acetamido] modification

| SEQ ID No. | Sequence | Mass Calcd | Mass Found | X$^a$ (min.) |
|---|---|---|---|---|
| 1 | 5'GCG T*T*T* T*T*T* T*T*T* T*GC G 3' | 5886.94 | 5886.89 | 18.83 |
| 2 | 5'CTC GTA CT*T* T*T*C CGG TCC 3' | 5797.69 | 5795.04 | 18.18 |
| 3 | 5'T*CC AGG T*GT* CCG CAT* C 3' | 5238.22 | 5236.56 | 17.81 |

$^a$HPLC retention time, Waters, C-4, 3.9 × 300 mm, A = 50 mM triethylammonium acetate pH = 7, B = acetonitrile 5 to 60% B in 55 min., flow 1.5 mL/min, λ = 260 nm; T* = 2'-O-[(N,N-Dimethyl)acetamido] $^{5Me}$U.

Example 43
5'-O-(4,4'-dimethoxytrityl)-2'-O-(2-N-methylacetamido)-5-methyluridine (63)

To a solution of Compound 4 dissolved in THF (8 mL) was added 40% $NH_2Me$-$H_2O$ (2.26 mL, 20 mmol) with stirring for 14 hours at ambient temperature. The solvent was evaporated in vacuo at 28° C. to give a foam which was purified by flash chromatography to give 599 mg (95%) of the title compound as a white foam.

$^1$H NMR ($CDCl_3$): δ 9.46 (bs, 1H), 7.71 (s, 1H), 7.31–6.82 (m, 13H), 5.91 (d, 1H, J 1', 2'=2.4 Hz), 4.45 (m, 1H), 4.37 ($q_{ab}$, 2H, $J_{a,b}$=15.2 Hz), 4.19 (m, 1H), 4.00 (m, 1H), 3.79 (s, 6H), 3.56 (m, 2H), 2.83 (m, 3H), 1.38 (s, 3H). $^{13}$C. NMR ($CDCl_3$): 67 170.8, 164.4, 158.9, 151.4, 144.6, 135.6, 135.5, 135.3, 130.3, 128.3, 128.2, 127.3, 113.5, 111.4, 88.5, 87.0, 84.1, 83.6, 70.0, 68.7, 61.9, 55.4, 26.6, 26.0, 12.0. LRMS (ES): 630.2 (M-H).

Example 44
General procedure for the synthesis of oligonucleotides having one or more 2'-O-{N-[2-(methylthio)ethyl] acetamido} modification modifications (post oligo synthesis)

An oligonucleotide is prepared having one or more nucleosides incorporated having 2'-O-methoxycarbonylmethylene functionalities using solid phase methodologies as previously illustrated. The CPG bound oligonucleotide having one or more 2'-O-methoxycarbonylmethylene functionalities is suspended in 50% 2-(methylthio)ethyl amine in methanol and kept at ambient temperature 24 hours. Under these conditions amine conjugation occurs by nucleophilic displacement of the methoxy group. The oligonucleotide is simultaneously cleaved from the CPG and protecting groups on exocyclic amino and phosphate groups are also removed. The mixture is filtered and evaporated to dryness to give the crude 5'-O-DMT oligonucleotide. The crude oligonucleotide is then passed through a Sephadex G-25 column and purified by HPLC (Waters, C-4 , 7.8×300 mm, A=50 mM triethyl-ammonium acetate, pH=7, B=acetonitrile 5 to 60% B in 55 Min. Flow 2.5 mL/min. Λ260 nm). Detritylation with aqueous 80% acetic acid and evaporation followed by desalting by HPLC using a Waters C-4 column gives the post synthesis modified oligonucleotide.

Oligonucleotides prepared using this procedure are shown in Table VI below.

TABLE VI

| SEQ ID NO. | Sequence | Mass Calcd | Mass Found |
|---|---|---|---|
| 5 | 5'-T**TT TTT TTT TTT 3' | | |
| 5 | 5'-T*TT TTT TTT TTT 3' | 4039.39$^a$ | 4038.48$^a$ |

T* = 2'-O-{N-[2-(methylthio)ethyl]acetamido} $^{5Me}$U.
T** = 2'-O-(methoxycarbonylmethylene) $^{5Me}$U $^a$ DMT On.

Example 45

Deprotection of oligomeric compounds containing 2'-O-acetamido modifications

CPG carrying 2'-O-acetamido oligonucleotides were suspended in aqueous NH, (30%solution) and kept at room temperature. Under these conditions the oligonucleotides were deprotected/cleaved from the CPG. Protected exocyclic amino groups on cytidine nucleosides (e.g. benzoyl, acetyl, etc.) were also deprotected simultaneously under these conditions. To the resulting mixture was added (to about 10% of the resulting volume) an aqueous solution of methylamine (40%) and the mixture was kept at room temperature for 22 hours to complete the deprotection of all groups (e.g. isobutyryl on guanidine nucleosides and benzoyl on adenosine nucleoside).

For a one μmole synthesis oligonucleotide bound to CPG was suspended in aqueous $NH_3$ (1.8 mL, 30 wt %) and kept at room temperature for 2 hours. To this aqueous methylamine (0.2 mL, 40 wt % solution) was added and kept at room temperature for an additional 22 hours to complete the deprotection.

This method was used to prepare oligonucleotide SEQ ID NO. 6, having the sequence CTC GTA CT*T* T*T*C CGG TCC, where T* represents a T that has a 2'-O—$CH_2$C(=O)—$N(CH_2)_2$ group (calc m+6099.83, found 6098.16).

What is claimed is:

1. A compound having the formula:

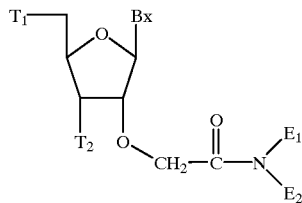

wherein:

Bx is an optionally protected heterocyclic base moiety;

each $T_1$ and $T_2$ is, independently, OH, a protected hydroxyl;

or one of $T_1$ and $T_2$ is OH or a protected hydroxyl and the other of $T_1$ and $T_2$ is a solid support or an activated phosphorus-containing substituent group;

each $E_1$ and $E_2$ is, independently, $C_1$–$C_{10}$ alkyl, or one of $E_1$ and $E_2$ is H and the other of $E_1$ and $E_2$ is —$CH_3$;

or each $E_1$ and $E_2$ is, independently, H, —$(CH_2)_m$—S—$R_4$ where m is from 1 to 10, —{$(CH_2)_{nn}$—N(H)}$_{nnn}$—$(CH_2)_{nn}NH_2$ where each nn is from 2 to 4 and nnn is from 2 to 10, a polypeptide having from 2 to 10 peptide linked amino acids, a folic acid moiety optionally bearing a linking group attaching said folic acid moiety from the α or γ carboxyl group to the 2'-substituent wherein said linking group is —N(H)—$(CH_2)_6$—, or a cholesterol moiety optionally bearing a linking group attaching said cholesterol moiety from the hydroxyl group to the 2'-substituent, wherein said linking group is —C(=O)—N(H)—$(CH_2)_6$—, provided that only one of $E_1$ and $E_2$ is H; and $R_4$ is H, $C_1$–$C_{10}$ alkyl, $C_2$–$C_{10}$ alkenyl, $C_2$–$C_{10}$ alkynyl, $C_6$–$C_{14}$ aryl or a thio protecting group.

2. The compound of claim 1 wherein each $E_1$ and $E_2$ is $C_1$–$C_{10}$ alkyl.

3. The compound of claim 1 wherein $E_1$ is H and $E_2$ is —$(CH_2)_m$—S—$R_4$.

4. The compound of claim 3 wherein $R_4$ is $C_1$–$C_{10}$ alkyl.

5. The compound of claim 4 wherein $R_4$ is methyl.

6. The compound of claim 1 wherein $E_2$ is {$(CH_2)_{nn}$—N(H)}$_{nnn}(CH_2)_{nn}NH_2$ where each nn is from 2 to 4 and nnn is from 2 to 10.

7. The compound of claim 6 wherein $E_2$ is —$(CH_2)_3$—N(H)—$(CH_2)_4$—N(H)—$(CH_2)_3$-$NH_2$ or —$(CH_2)_4$—N(H)—$(CH_2)_3$—$NH_2$.

8. The compound of claim 1 wherein $E_2$ is said polypeptide.

9. The compound of claim 8 wherein said polypeptide is Lys-Tyr-Lys, Lys-Trp-Lys or Lys-Lys-Lys-Lys.

10. The compound of claim 1 wherein $E_2$ is a linked folic acid or 5-methyl-tetrahydrofolic acid moiety.

11. The compound of claim 1 wherein $E_2$ is a cholesterol moiety.

12. The compound of claim 1 wherein said heterocyclic base moiety is a purine or a pyrimidine radical.

13. The compound of claim 12 wherein said heterocyclic base moiety is adeninyl, cytosinyl, 5-methylcytosinyl, thyminyl, uracilyl, guaninyl or 2-aminoadeninyl.

14. The compound of claim 1 wherein $T_1$ is a protected hydroxyl and $T_2$ is an activated phosphorus-containing substituent group.

15. An oligomeric compound comprising at least one moiety of the formula:

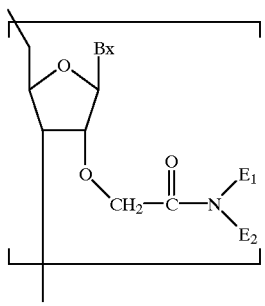

wherein:
Bx is an optionally protected heterocyclic base moiety;
each $E_1$ and $E_2$ is, independently, $C_1$–C10 alkyl, or one of $E_1$ and $E_2$ is H and the other of $E_1$ and $E_2$ is $CH_3$;
or each $E_1$ and $E_2$ is, independently, H, —$(CH_2)_m$—S—$R_4$ where m is from 1 to 10, —{$(CH_2)_{nn}$—N(H)}$_{nnn}$—$(CH_2)_{nn}NH_2$ where each nn is from 2 to 4 and nnn is from 2 to 10, a polypeptide having from 2 to 10 peptide linked amino acids, a folic acid moiety optionally bearing a linking group attaching said folic acid moiety from the α or γ carboxyl group to the 2'-substituent wherein said linking group is —N(H)—$(CH_2)_6$—, or a cholesterol moiety optionally bearing a linking group attaching said cholesterol moiety from the hydroxyl group to the 2'-substituent, wherein said linking group is —C(=O)—N(H)—$(CH_2)_6$—, provided that only one of $E_1$ and $E_2$ is H; and
$R_4$ is H, $C_1$–$C_{10}$ alkyl, $C_2$–$C_{10}$ alkenyl, $C_2$–$C_{10}$ alkynyl, $C_6$–$C_{14}$ aryl or a thio protecting group.

16. The oligomeric compound of claim 15 wherein each $E_1$ and $E_2$ is $C_1$–$C_{10}$ alkyl.

17. The oligomeric compound of claim 15 wherein $E_1$ is H and $E_2$ is —$(CH_2)_m$—S—$R_4$.

18. The oligomeric compound of claim 17 wherein $R_4$ is $C_1$–$C_{10}$ alkyl.

19. The oligomeric compound of claim 18 wherein $R_4$ is methyl.

20. The oligomeric compound of claim 15 wherein $E_2$ is —{$(CH_2)_{nn}$—N(H)}$_{nnn}$—$(CH_2)_{nn}NH_2$ where each nn is from 2 to 4 and nnn is from 2 to 10.

21. The oligomeric compound of claim 20 wherein $E_2$ is —$(CH_2)_3$—N(H)—$(CH_2)_4$—N(H)—$(CH_2)_3$-$NH_2$ or —$(CH_2)_4$—N(H)—$(CH_2)_3$—$NH_2$.

22. The oligomeric compound of claim 15 wherein $E_2$ is a linked folic acid or 5-methyl-tetrahydrofolic acid moiety.

23. The oligomeric compound of claim 15 wherein $E_2$ is a cholesterol moiety.

24. The oligomeric compound of claim 15 wherein $E_2$ is said polypeptide.

25. The oligomeric compound of claim 24 wherein said polypeptide is Lys-Tyr-Lys, Lys-Trp-Lys or Lys-Lys-Lys-Lys.

26. The oligomeric compound of claim 15 wherein said heterocyclic base moiety is a purine or a pyrimidine radical.

27. The oligomeric compound of claim 26 wherein said heterocyclic base moiety is adeninyl, cytosinyl, 5-methylcytosinyl, thyminyl, uracilyl, guaninyl or 2-aminoadeninyl.

28. The oligomeric compound of claim 15 comprising from about 5 to about 50 nucleosides.

29. The oligomeric compound of claim 15 comprising from about 8 to about 30 nucleosides.

30. The oligomeric compound of claim 15 comprising from about 15 to about 25 nucleosides.

31. A process for preparing an oligomeric compound comprising the steps of:
(a) selecting a solid support bound oligomeric compound having at least one moiety of the formula:

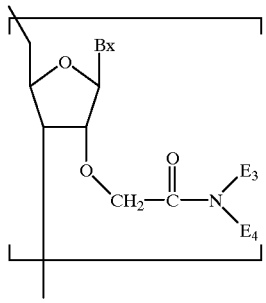

wherein:
Bx is an optionally protected heterocyclic base moiety;
each $E_3$ and $E_4$ is, independently, H, a nitrogen protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, wherein said substitution is $OR_3$, $SR_3$, $NH_3^+$, $N(R_3)$ $(R_4)$, guanidino, —$(CH_2)_{nn}$—C(=O)—OH, —$(CH_2)_{nn}$—C(=O)—$NH_2$ or —$(CH_2)_{nn}$—C(=O)—O—$(CH_2)_{nn}$—$CH_3$, where each nn is from 1 to 10;
each $R_3$ and $R_4$ is, independently, H, $C_1$–$C_{10}$ alkyl, $C_2$–$C_{10}$ alkenyl, $C_2$–$C_{10}$ alkynyl, $C_6$–$C_{14}$ aryl, a nitrogen protecting group, a thio protecting group, or $R_3$ and $R_4$, together, are a nitrogen protecting group;
or $R_3$ and $R_4$ are joined in a ring structure that optionally includes an additional heteroatom selected from N and O;
(b) contacting said solid support bound oligomeric compound with a solution of ammonium hydroxide at ambient temperature to give a basic mixture; and
(c) adding a solution of methylamine to said basic mixture at ambient temperature to provide said oligomeric compound.

32. The process of claim 31 wherein said contacting with said ammonium hydroxide is for about one hour to about 3 hours.

33. The process of claim 32 wherein said contacting is for about 2 hours.

34. The process of claim 31 wherein the concentration of ammonium hydroxide in said solution is from about 20% to saturated.

35. The process of claim 34 wherein the concentration of ammonium hydroxide in said solution is saturated.

36. The process of claim 31 wherein said ambient temperature is from about 15° C. to about 30° C.

37. The process of claim 36 wherein said ambient temperature is from about 20° C. to about 25° C.

38. The process of claim 31 wherein said solution of methylamine is from about 30% to about 50% methylamine in water.

39. The process of claim 38 wherein said solution of methylamine is 40%.

40. The process of claim 31 wherein step (c) is performed over a period of from about 10 hours to about 30 hours.

41. The process of claim 40 wherein step (c) is performed over a period of about 26 hours.

42. The process of claim 31 wherein said solid support is controlled pore glass (CPG).

43. The compound of claim 1 wherein $E_1$ and $E_2$ are $CH_3$.

44. The compound of claim 1 wherein $E_1$ is H and $E_2$ is $CH_3$.

45. The oligomeric compound of claim 15 wherein $E_1$ and $E_2$ are $CH_3$.

46. The oligomeric compound of claim 15 wherein $E_1$ is H and $E_2$ is $CH_3$.

* * * * *

UNITED STATES PATENT AND TRADEMARK OFFICE
CERTIFICATE OF CORRECTION

PATENT NO. : 6,147,200
DATED : November 14, 2000
INVENTOR(S) : Muthiah Manoharan et al.

It is certified that error appears in the above-identified patent and that said Letters Patent is hereby corrected as shown below:

Column 13,
Line 26, "C" should be -- O --.

Column 19,
Line 35, "04-02" should be -- $O_4 - O_+$ --.

Column 25,
Line 39, "ashed" should be -- washed --

Column 34,
Line 52, "77.44" should be -- 7.44 --.

Signed and Sealed this

Thirtieth Day of October, 2001

Attest:

NICHOLAS P. GODICI
*Attesting Officer*    *Acting Director of the United States Patent and Trademark Office*